United States Patent
Cimenser et al.

(10) Patent No.: US 10,564,720 B2
(45) Date of Patent: Feb. 18, 2020

(54) USER INPUT VALIDATION AND VERIFICATION FOR AUGMENTED AND MIXED REALITY EXPERIENCES

(71) Applicant: DAQRI, LLC, Los Angeles, CA (US)

(72) Inventors: Aylin Cimenser, Santa Monica, CA (US); Hani Awni, Riverwoods, IL (US); Frank Chester Irving, Jr., Woodland Hills, CA (US); Stefanie A. Hutka, Los Angeles, CA (US)

(73) Assignee: DAQRI, LLC, Los Angeles, CA (US)

( * ) Notice: Subject to any disclaimer, the term of this patent is extended or adjusted under 35 U.S.C. 154(b) by 72 days.

(21) Appl. No.: 15/807,032

(22) Filed: Nov. 8, 2017

(65) Prior Publication Data

US 2018/0188807 A1 Jul. 5, 2018

Related U.S. Application Data

(60) Provisional application No. 62/441,249, filed on Dec. 31, 2016.

(51) Int. Cl.
| | |
|---|---|
| *G06F 3/01* | (2006.01) |
| *A61B 5/00* | (2006.01) |
| *A61B 5/0484* | (2006.01) |
| *H04W 84/18* | (2009.01) |
| *G06F 3/0484* | (2013.01) |
| *G06F 3/16* | (2006.01) |

(52) U.S. Cl.
CPC .......... *G06F 3/015* (2013.01); *A61B 5/04842* (2013.01); *A61B 5/04845* (2013.01); *A61B 5/6803* (2013.01); *G06F 3/016* (2013.01); *G06F 3/0484* (2013.01); *G06F 3/167* (2013.01); *H04W 84/18* (2013.01)

(58) Field of Classification Search
CPC .............. A61B 5/0022; A61B 5/04842; A61B 5/04845; A61B 5/18; A61B 5/6803; G02B 27/017; G06F 3/011; G06F 3/013; G06F 3/015; G06F 3/016; G06F 3/0484; G06F 3/167; H04W 84/18
See application file for complete search history.

(56) References Cited

U.S. PATENT DOCUMENTS

| | | | | |
|---|---|---|---|---|
| 2005/0017870 | A1* | 1/2005 | Allison | G06F 3/015 340/4.13 |
| 2011/0144522 | A1* | 6/2011 | Sajda | A61B 5/048 600/544 |
| 2014/0228701 | A1* | 8/2014 | Chizeck | A61B 5/04012 600/544 |
| 2014/0333529 | A1* | 11/2014 | Kim | G06F 3/04842 345/156 |
| 2014/0347265 | A1* | 11/2014 | Aimone | G09G 3/003 345/156 |

(Continued)

*Primary Examiner* — Hong Zhou
(74) *Attorney, Agent, or Firm* — Schwegman Lundberg & Woessner, P.A.

(57) ABSTRACT

A head-mounted display (HMD) system includes an HMD device worn on a head of a user. The HMD device incorporates electroencephalography (EEG) interfaces for monitoring the brain of the human subject during interaction with the HMD device. Fluctuations in electrical potential that are observed via the EEG interfaces may be used to detect event-related potentials (ERPs). The HMD system may programmatically perform one or more operations in response to detecting ERPs.

18 Claims, 15 Drawing Sheets

(56) References Cited

U.S. PATENT DOCUMENTS

| | | | |
|---|---|---|---|
| 2015/0310750 A1* | 10/2015 | Glaunsinger | A61B 5/0075 434/258 |
| 2016/0077547 A1* | 3/2016 | Aimone | G06F 3/012 345/8 |
| 2016/0113587 A1* | 4/2016 | Kothe | A61B 5/7203 600/301 |

* cited by examiner

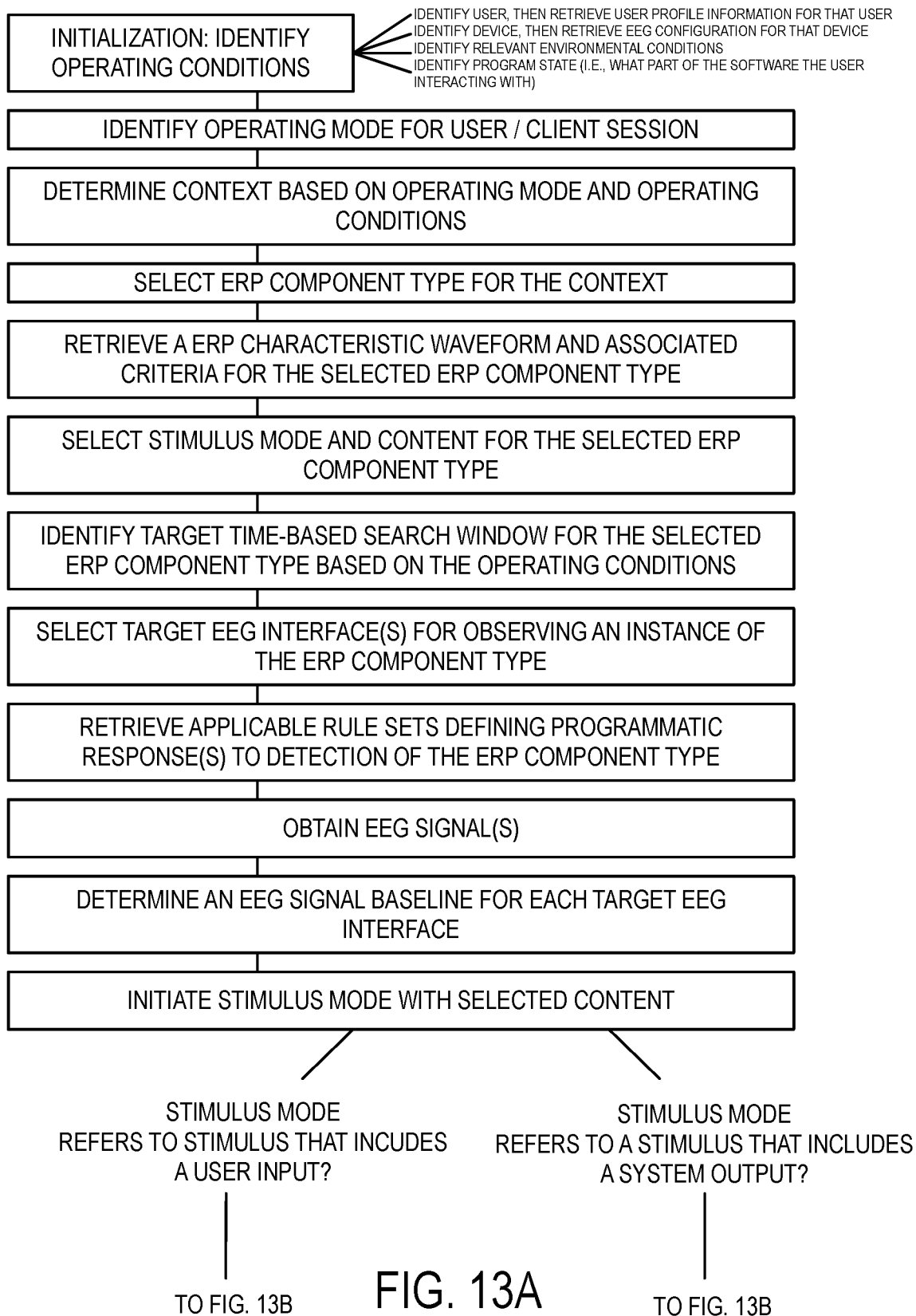

USER INPUT VALIDATION AND VERIFICATION FOR AUGMENTED AND MIXED REALITY EXPERIENCES

RELATED APPLICATION

This application claims the benefit of priority of U.S. Provisional Application No. 62/441,249, filed Dec. 31, 2016, which is herein incorporated by reference in its entirety.

TECHNICAL FIELD

The subject matter disclosed herein generally relates to a head-mounted display (HMD) system. Specifically, the present disclosure addresses systems for monitoring attention, comprehension, and drowsiness of a user operating the head-mounted display system.

BACKGROUND

Electroencephalography (EEG) refers to a technique for monitoring electrical activity of the brain of a living organism—typically the brain of a human subject. Fluctuations in electrical potential may be observed at various locations or regions of the brain via a set of EEG interfaces that are spatially distributed relative to the subject's head. These EEG interfaces may take the form of non-invasive electrodes that are placed near or in contact with the scalp at various locations.

An event-related potential (ERP) refers to a response of the brain to a stimulus event that has been perceived by the subject. ERPs may be detected via EEG as fluctuations in electrical potential observed during a period of time following the subject's perception of the stimulus event. With respect to human subjects, temporal fluctuations in electrical potentials observed at particular locations relative to the head of the human subject and within time-locked search windows relative to onset of the stimulus event enable such ERPs to be detected and identified.

A range of ERPs, referred to as ERP components, have been experimentally observed across large populations of human subjects in a consistent manner with respect to the type of stimulus, suggesting the universality of such ERPs in humans. Many ERP components have been characterized with respect to the type of stimulus event that elicits an observable fluctuation in electrical potential, and these fluctuations have been assigned names by the scientific community within a nomenclature that enables consistent identification and discussion of the ERP components.

BRIEF DESCRIPTION OF DRAWINGS

FIGS. 13A and 13B is a flow diagram depicting an example method that may be implemented with respect to detection of ERP components.

DETAILED DESCRIPTION

Head mounted display (HMD) devices refer to electronic devices that feature one or more graphical display(s) and are wearable upon the head of a human subject (i.e., a user). HMD devices may include left and right near-eye graphical displays that support augmented reality (AR), mixed reality (MR), or virtual reality (VR) experiences in the visual domain. Auditory and/or haptic stimulus provided by the HMD device or associated peripheral devices may further support these visual experiences.

For HMD devices, augmented reality and mixed reality may be achieved through two primary techniques. As a first example, the near-eye graphical displays take the form of transparent display panels through which the user may view the real-world environment. Graphical content representing virtual objects may be presented on or within the transparent panels to provide the appearance of the virtual objects being physically present within the real-world environment. As a second example, the near-eye graphical displays may take the form of fully immersive display devices that occlude the user's field of vision. A camera view that approximates the user's field of vision of the real-world environment may be presented by these display devices integrated with graphical content representing virtual objects to provide the appearance of the virtual objects being physically present within the real-world environment.

Figure 1:
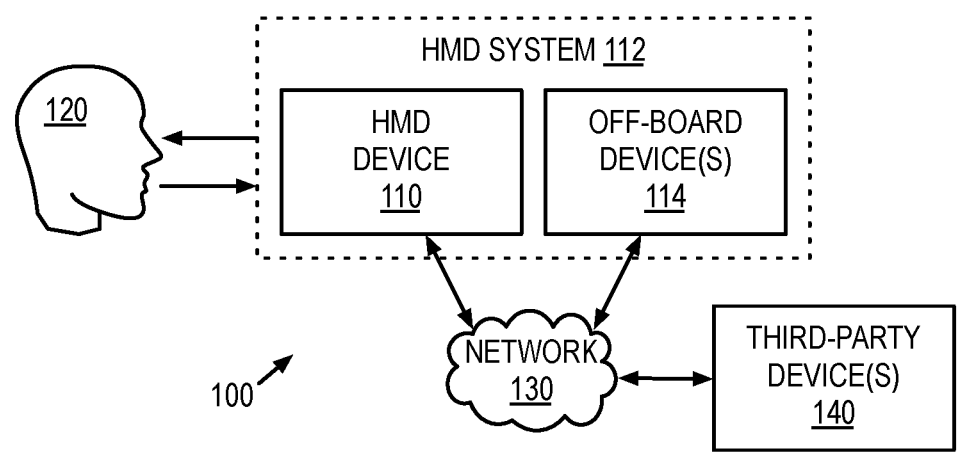
FIG. 1 is a schematic diagram depicting an example use environment that includes a head-mounted display (HMD) device that is wearable by a human subject.

FIG. 1 is a schematic diagram depicting an example use environment 100 that includes a head-mounted display (HMD) device 110 that is wearable by a human subject (i.e., a user), represented schematically at 120. HMD device 110 may include one or more graphical displays operable to visually provide an augmented reality, mixed reality, or virtual reality experience to user 120. An example HMD device is described in further detail with reference to FIGS. 10 and 11.

HMD device 110 may form part of an HMD system 112 that further includes one or more off-board device(s) 114. Off-board device(s) 114 may include one or more computing device(s), sensor device(s), and/or other HMD device(s), as non-limiting examples. Off-board device(s) 114 may communicate between or among each other or with HMD device 110 via a communications network 130 or a portion thereof. Communications network 130 may include one or more personal area network (PAN) components, local area network (LAN) components, and/or wide area network (WAN) components, and may support wired and/or wireless communications over one or more communications protocol(s). HMD device 110 and/or off-board device(s) 114 of HMD system 112 may communicate with one or more third-party device(s) 140 that are external the HMD system via communications network 130 or a portion thereof.

As described in further detail herein, HMD device 110 may include one or more electroencephalography (EEG) interfaces by which event-related potentials (ERPs) may be observed with respect to brain responses of a human subject. EEG refers to a technique for monitoring electrical activity of the brain of a living organism—typically the brain of a human subject. Fluctuations in electrical potential may be observed at various locations or regions of the brain via a set of EEG interfaces that are spatially distributed relative to the subject's head. These EEG interfaces may take the form of non-invasive electrodes that are placed near or in contact with the scalp at various locations.

An event-related potential (ERP) refers to a response of the brain to a stimulus event that has been perceived by the subject. ERPs may be detected via EEG as fluctuations in electrical potential observed during a period of time following the subject's perception of the stimulus event. With respect to human subjects, temporal fluctuations in electrical potentials observed at particular locations relative to the head of the human subject and within time-locked search windows relative to onset of the stimulus event enable such ERPs to be detected and identified.

A range of ERPs, referred to as ERP components, have been experimentally observed across large populations of human subjects in a consistent manner with respect to the type of stimulus, suggesting the universality of such ERPs in humans. Many ERP components have been characterized with respect to the type of stimulus event that elicits an observable fluctuation in electrical potential, and these fluctuations have been assigned names by the scientific community within a nomenclature that enables consistent identification and discussion of the ERP components. Non-limiting examples of ERPs are described in further detail with reference to FIGS. 3A, 3B, 3C, and 3D.

While the use of EEG is described within the context of an HMD device, it will be understood that a wearable EEG device that does not include integrated graphical displays may instead be used in combination with one or more peripheral graphical display device(s) to implement some or all aspects of the present disclosure. Within this context, the EEG device may interface with the peripheral graphical display device(s) via a communications network (e.g., 130) or a portion thereof.

Figure 2:
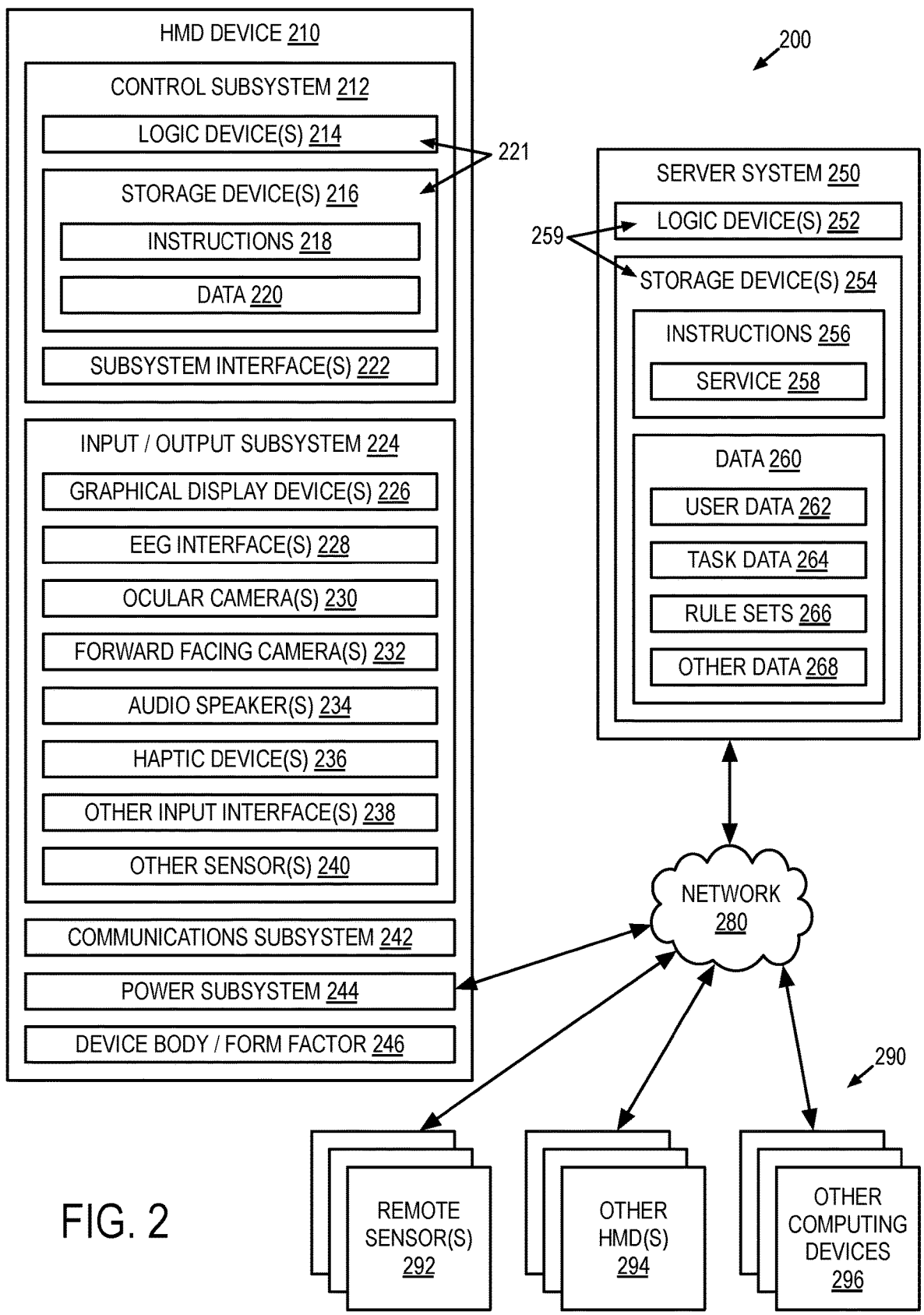
FIG. 2 is a schematic diagram depicting an example computing system that includes an HMD device.

FIG. 2 is a schematic diagram depicting an example computing system 200 that includes an HMD device 210. HMD device 210 is a non-limiting example of previously described HMD device 110 of FIG. 1, as described in further detail. Various components of HMD device 210 are represented schematically in FIG. 2. These components may be integrated with HMD device 210 or may take the form of peripheral devices that interface with HMD device 210.

HMD device 210 may include a control subsystem 212. Control subsystem 212 may include one or more logic device(s) 214, one or more storage device(s) 216, and/or one or more subsystem interface(s) 222. Storage device(s) 216 may have instructions 218 and/or data 220 stored thereon. Instructions 218 are executable by logic device(s) 214 to perform or otherwise implement the various operations, processes, functions, or tasks described herein with respect to an HMD device (or a wearable EEG device). For example, instructions 218 may define an operating system and/or on-board program that is implemented by logic device(s) of HMD device 210, enabling user interaction with the HMD device and/or the greater HMD system. Collectively logic device(s) 214 and storage device(s) 216 may take the form of an on-board computing device 221. On-board computing device 221 may be referred to as being programmed with instructions 218 when carrying instructions 218 in on-board data storage device(s) 216 and/or executing instructions 218 at logic device(s) 214.

Subsystem interface(s) 222 may operatively interface with the various other subsystems or components of HMD device 210. Subsystem interface(s) 222 may include or incorporate a computer bus, in an example, over which these various subsystems or components may communicate, share electrical power resources, or otherwise interact with each other.

HMD device 210 may further include an input/output subsystem 224, a communications subsystem 242, a power subsystem 244, and/or a device body/form factor 246. Input/output subsystem 224 may include one or more input device(s) and one or more output device(s), including as examples: one or more graphical display device(s) 226, one or more EEG interface(s) 228, one or more ocular camera(s) 230, one or more forward facing camera(s) 232, one or more audio speaker(s) 234, one or more haptic device(s) 236, one or more other input interface(s) 238, and/or other sensor(s) 240 (e.g., a GPS, GNSS, or other positioning sensor system enabling determination of the geographic position of the HMD device). Graphical display device(s) 226 may take the form of near-eye graphical display devices (e.g., left-eye and right-eye graphical display devices) upon which augmented reality or mixed reality content may be presented. Visual stimulus in the form of textual or non-textual graphical information may be presented to the user via graphical display device(s) 226. Auditory stimulus in the form of textual or non-textual sound information may be presented to the user via audio speaker(s) 234. Haptic stimulus representing textual or non-textual haptic information may be presented to the user via haptic device(s) 236.

Each EEG interface of EEG interface(s) 228 may include a respective electrode, associated amplifier component, associated analog-to-digital conversion component, and associated electrical power source, among other suitable components for obtaining EEG signals. Electrodes of the EEG interfaces may be passive (with sufficient contact with the human subject and/or low impedance) or active. The electrodes typically penetrate the hair of the human subject to contact the scalp or skin at respective locations relative to the head. In an example, EEG interfaces 228 may include frontal, central, and parietal EEG electrodes, among other suitable electrode locations. One or more of the EEG interfaces may include a reference electrode to which other electrodes of the EEG interfaces may be referenced. For example, one or more reference electrodes may be located at or near a mastoid, earlobe, nose tip, or other scalp location, etc. However, reference electrodes may be omitted in at least some implementations, such as with active electrodes.

Communications subsystem 242 may include one or more wireless interface devices to transmit and/or receive wireless communications. Examples of wireless interface devices include a wireless receiver, a wireless transmitter, or a wireless transceiver, as well as associated signal processing components. Wireless interface devices may support wireless communications over any suitable wireless protocol, such as Wi-Fi, Bluetooth, RFID, NFC, LTE, etc., over a personal area network, local area network, and/or wide area network components of a communications network. Wireless interface devices may utilize radio frequency and/or other suitable wireless frequency ranges, as well as electromagnetic fields in the case of RFID, to communicate wirelessly with other computing devices or electronic hardware. Communication subsystem 242 may include one or more wired interface devices. Examples of wireless interface devices include electronic connectors and associated signal processing components. Such electronic connectors may include support for exchanging an electrical ground reference, electrical power, and/or data/signal connections with a corresponding electronic connector of another device or power source.

Power subsystem 244 may include one or more on-board energy storage device(s) (e.g., a battery) for powering the HMD device and its various subsystems and components without requiring physical connection to an external power source. Power subsystem 244 may include an electronic connector for receiving electrical power from external power sources and other suitable components for providing power conditioning and distribution.

Figure 10:
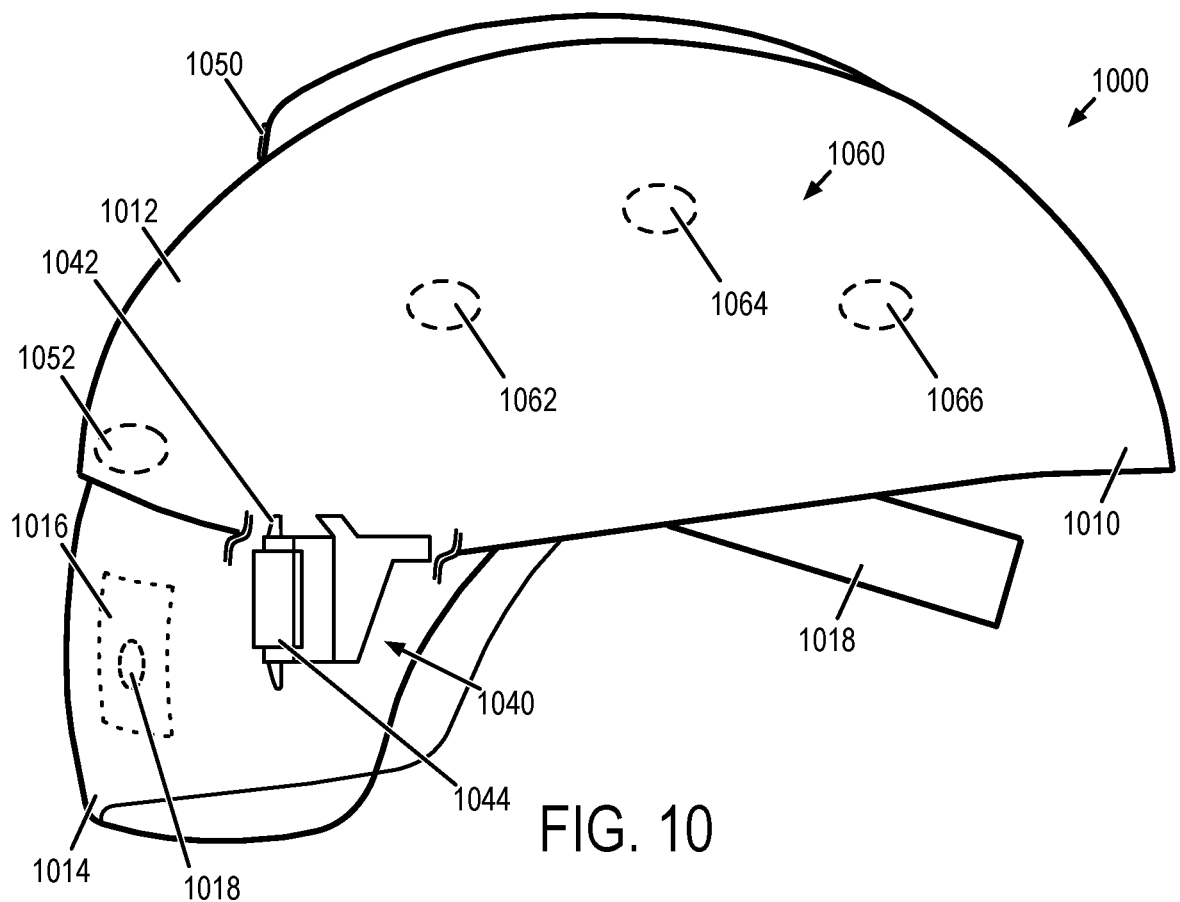
FIG. 10 depicts an example head mounted display (HMD) device that is wearable upon a head of a human subject.
Figure 11:
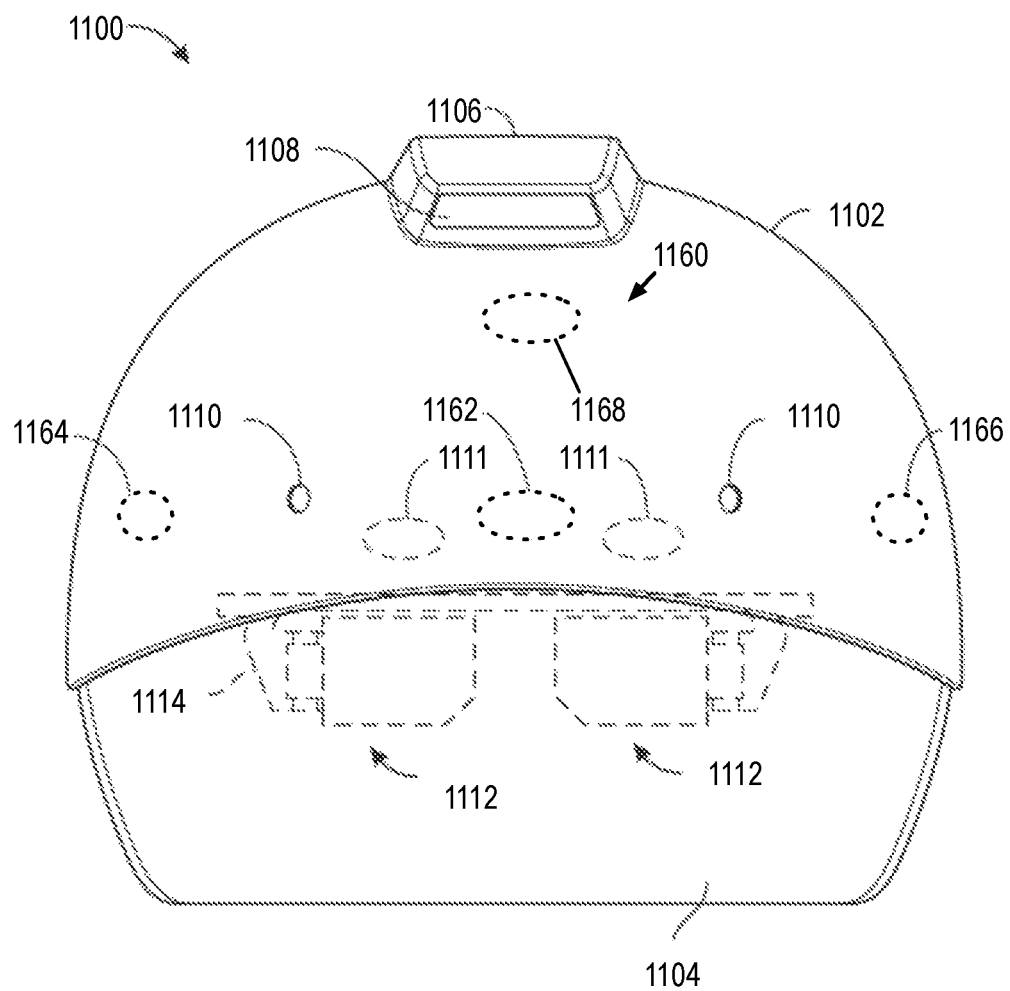
FIG. 11 depicts additional aspects of an example HMD device.

Device body/form factor 246 may include any suitable form, depending on implementation, for mounting and/or enclosing the various subsystems and components. For example, device body/form factor 246 may take the form of a helmet that is worn upon the head of a human subject, with a visor or see-through display panel that contains one or more near-eye graphical displays. FIGS. 10 and 11 depict non-limiting examples of an HMD device form factor. However, other suitable form factors may be used, depending on implementation.

Computing system 200 may further include a server system 250. Server system 250 is a non-limiting example of off-board device(s) 114 of FIG. 1. For example, server system 250 may form part of an HMD system with HMD device 210, as previously described with reference to HMD system 112 of FIG. 1. Server system 250 may include one or more server devices. Two or more server devices of server system 250 may co-located and/or two or more server devices of server system 250 may be geographically distributed. Server system 250 may support coordinated operation with many HMD devices worn by many different users, in at least some examples.

Server system 250 may include one or more logic device(s) 252, and one or more storage device(s) 254. Storage device(s) 254 may have instructions 256 and/or data 260 stored thereon. Instructions 256 are executable by logic device(s) 252 to perform or otherwise implement the various operations, processes, functions, or tasks described herein with respect to a server system or other off-board computing device. Collectively, logic device(s) 252 and storage device(s) 254 may take the form of one or more computing device(s) 259 that are incorporated into one or more server device(s). Computing device(s) 259 may be referred to as being programmed with instructions 256 when carrying instructions 256 in data storage device(s) 254 or executing instructions 256 at logic device(s) 252.

As an example, instructions 256 may include or take the form of a program or set of programs that defines a service 258. Within the context of a networked server system, service 258 may be referred to as a hosted service or cloud-based service with which HMD 210 and/or other networked devices may communicate or otherwise interact. For example, HMD device 210 and server system 250 may communicate via a communications network 280. Communications network 280 is a non-limiting example of previously described communications network 130 of FIG. 1. For example, communications network 280 may include wide area network components such as the Internet or a portion thereof, as well as wireless edge network components.

Examples of data 260 may include user data 262, task data 264, rule sets 266, and other data 268. User data 262 may include user profiles for users that have registered with the HMD system. Task data 264 may include task profiles for tasks that can be assigned to a user, such as within a work environment. Rule sets 266 may define operations that are to be programmatically performed by the server system or deployed to the HMD device to be performed responsive to a particular set of conditions. Other data 268 may include measurement data obtained from HMD devices, such as HMD device 210. An example data structure is described in further detail with reference to FIG. 12.

Instances of data 260 or portions thereof may reside at or may be communicated to or from other devices, such as HMD device 210. For example, instances of data included in a user profile or a task profile for a user may be distributed or otherwise made accessible to the HMD device or to a user of the HMD device, and may be temporarily or persistently stored within data 220 of storage device(s) 216 residing on-board the HMD device. Service 258 may support an access control feature that enables users to login to their respective user account of the service by providing login credentials. Following login, the service may identify a particular user as being associated with a particular HMD device. Service 258 may distinguish among many users of the service and their respective devices to support many concurrent client sessions. Service 258 may interface with on-board programs operating at HMD device 210 via an application programming interface (API) that forms part of the service or part of the on-board program.

Computing system 200 may include a variety of other devices 290, such as one or more remote sensor(s) 292, one or more other HMD(s) 294, and one or more other computing device(s) 296. Depending on implementations, some of devices 290 may be examples of third-party device(s) 140 of FIG. 1 that are external the HMD system. However, some or all of devices 290 may represent examples of off-board device(s) 114 of FIG. 1 that collectively form part of HMD system 112 with one or more HMD devices.

Within the field of EEG, the "10-20 system" defines a standardized nomenclature that describes a variety of surface locations of a human head. Within this nomenclature, various locations on the surface (e.g., scalp) of the head may be described by an alphanumeric code, which may take the form of a combination of a first character (typically a letter represented in upper case) that defines a brain lobe or other region of the head, and a second character (typically a number or a second letter represented in lower case) that defines a hemisphere or other region relative to a midline of the head. With regards to the first character, the letters F, T, C, P, O, A refer to the following regions: frontal lobe, temporal lobe, central region, parietal lobe, occipital lobe, and earlobe, respectively. With regards to the second character, even numbers (e.g., 2, 4, 6, 8) refer to respective locations on the right hemisphere of the head and odd numbers (e.g., 1, 3, 5, 7) refer to respective locations on the left hemisphere of the head. Also with regards to the second character, the letter "z" corresponding to the number "zero" or "0" refers to a location along a midline of the head. Furthermore, the code "Fp" refers to the frontal polar location of the head, and the code "Pg" refers to nasopharyngeal location.

EEG interfaces may include corresponding electrodes that are spatially distributed along the scalp or other surfaces of the head of a human subject to provide a variety of different observation points for observing fluctuations in electrical potential. For example, a set of EEG interfaces may be spatially distributed at or near locations corresponding to Fpz, Fz, Cz, etc., to use the nomenclature of the 10-20 system, among other suitable electrode locations. Fluctuations in electrical potential occurring within the head of the human subject may be observed via these spatially distributed EEG interfaces. Each observation point provides a different measurement of electrical potential that reflects brain activity of the human subject proximate to and from the perspective of that observation point.

Time-based measurements of electrical potential observed via the EEG interfaces over a period of time may be captured and analyzed to identify characteristic fluctuations in electrical potential that correspond to an event-related potential (ERP). An ERP refers to a response of the brain of a human subject that results from a sensory-based event, cognitive-based event, and/or motor-based event (collectively referred to as stimulus events). An ERP may include one or more components that are related to and identifiable from positive or negative deflections (relative to a baseline) in the electrical potential that are present in a time-based waveform that is observed at a particular observation point. Non-limiting examples of ERP components are described in further detail with reference to FIGS. 3A, 3B, 3C, and 3D.

Fluctuations in electrical potential observed via at last one electrode of an EEG interface may take the form of positive and/or negative deflections in electrical potential relative to a baseline. A waveform representing a deflection in electrical potential may include a beginning, an end, and a maximum value or peak located between the beginning and end of the waveform. Because the EEG signal representing the observed electrical potential is a time-varying signal, the beginning, end, and absolute maximum value may be associated with time values within a global time frame and within a time frame that is keyed to onset of the stimulus event that elicited the response. EEG signals obtained from a set of two or more EEG interfaces may be time-locked relative to each other to enable comparison of electrical potential observations between or among the EEG interfaces.

Figure 3A:
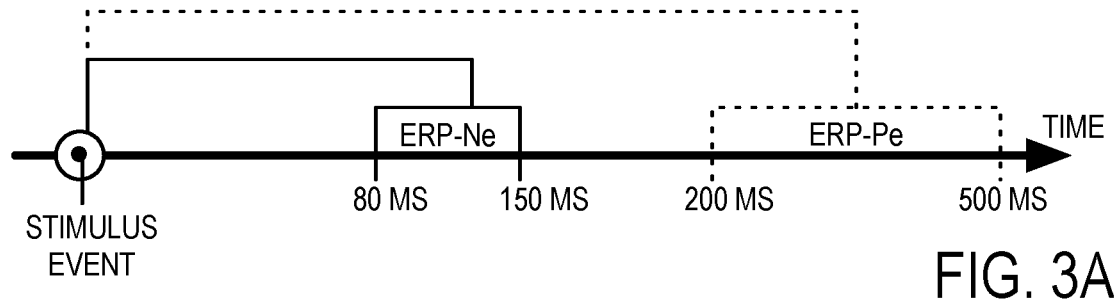
FIG. 3A is a timeline depicting an example relationship between a stimulus event and resulting fluctuations in electrical potential indicative of an ERP, including an error-related negativity (ERP-Ne) component and an error-related positivity (ERP-Pe) component observed via one or more EEG interface(s).

FIG. 3A is a timeline depicting an example relationship between a stimulus event and resulting fluctuations in electrical potential indicative of an ERP, including an error-related negativity (ERP-Ne) component and an error-related positivity (ERP-Pe) component observed via one or more EEG interface(s).

The ERP-Ne and/or ERP-Pe components may be observed with respect to a human subject following onset of a stimulus event. Within the context of ERP-Ne and ERP-Pe components, the stimulus event may, for example, include an erroneous or anomalous action performed by the human subject (e.g., a button press or other selection action) or an event perceived by the human subject that contains an error or anomaly. The ERP-Ne component may be observed even if the human subject is consciously unaware of the error or anomaly. By contrast, the ERP-Pe component may be observed following the ERP-Ne if or when the human subject is consciously aware of the error or anomaly. Thus, a human response to a stimulus event that includes an observed ERP-Ne component without observing a corresponding ERP-Pe component may be indicative of the human subject performing an erroneous or anomalous action or perceiving an erroneous or anomalous event without consciously recognizing that the stimulus event contained the error or anomaly.

As depicted in FIG. 3A, the ERP-Ne component of the ERP may be observed as a deflection in electrical potential from a baseline that occurs approximately 80-150 milliseconds (ms) following onset of the stimulus event. In certain contexts, such as with a simple action (e.g., a button press or other selection action), the deflection in electrical potential representing the ERP-Ne component may begin prior to the user initiating the action, with the peak deflection in electrical potential being observed approximately 80-100 ms following the subject initiating the action. The 80-150 ms time period, the 80-100 ms period, or other suitable time period for detecting the ERP-Ne component may be referred to as an ERP-Ne search window. It will be appreciated that these time ranges represents example time ranges. In real-world implementations, the time range for observing the ERP-Ne component may vary with operating conditions, such as the type of stimulus event, the content of the stimulus event, the sensory modality for perceiving the stimulus event, content or environmental conditions, and characteristics or conditions of the human subject (e.g., age, health, skill level/experience, etc.).

For the ERP-Ne component, the deflection in electrical potential typically takes the form of a negative deflection from a baseline electrical potential observed via at least one electrode of an EEG interface. Example ranges for this negative deflection may include −0.01 volts to −12.00 microvolts. However, other voltage ranges may be observed depending, for example, on the previously described operating conditions that may also influence timing of the observed deflection in electrical potential. A spatial distribution of the ERP-Ne component typically lies over frontal-central regions of the scalp and typically reaches a maximum amplitude in a region over the supplementary motor area of the brain. An electrode of an EEG interface that is located at or near a frontal location (e.g., Fp) or a fronto-central location (e.g., Fz) relative to the head of a human subject may be used to observe the ERP-Ne component. However, other suitable locations (e.g., right or left of the midlines and/or forward or rearward of the Fp or Fz locations) may be used to observe the ERP-Ne component.

An Ne-characteristic fluctuation in electrical potential may be collectively defined by (1) an expected time range (e.g., 80-150 ms) for observing a deflection or a feature of the deflection representing the ERP-Ne component, (2) an expected direction of the deflection (e.g., negative) relative to a baseline, (3) an expected magnitude range of the deflection (e.g., −0.01 volts to −12.00 microvolts), (4) an expected location relative to the head of the human subject (e.g., an expected EEG interface of a spatially distributed set of EEG interfaces) by which the deflection in electrical potential is observed, and (5) presence of a subsequently observed ERP-Pe component within a time-locked EEG signal. As described in further detail with reference to FIGS. 4 and 5, this Ne-characteristic fluctuation in electrical potential may be used to detect whether an ERP-Ne component is present within an EEG signal.

The ERP-Pe component of the ERP may be observed after the ERP-Ne component at approximately 200-500 ms following onset of the stimulus event. This 200-500 ms time period or other suitable time period for detecting the ERP-Pe component may be referred to as an ERP-Pe search window. It will be appreciated that this time range represents an example time range for ERP-Pe, as various operating conditions may influence the timing of fluctuations in electrical potential indicative of the ERP-Pe component.

For the ERP-Pe component, the deflection in electrical potential typically takes the form of a positive deflection from a baseline electrical potential observed via at least one electrode of an EEG interface. The ERP-Pe component typically presents as a positive slowly growing and/or decaying waveform of electrical potential (as compared to the ERP-Ne component) with a maximum value or peak occurring at approximately 300 ms or later following onset of the stimulus event. A spatial distribution of the ERP-Pe component typically lies over parietal and/or centro-parietal regions of the scalp. An electrode of an EEG interface that is located at or near a central location (e.g., Cz) or a parietal location (e.g., Pz) relative to the head of a human subject may be used to observe the ERP-Pe component. However, other suitable locations (e.g., right or left of the midline and/or forward or rearward of the Cz or Pz locations) may be used to observe the ERP-Pe component.

A Pe-characteristic fluctuation in electrical potential may be collectively defined by one or more of the following: (1) an expected time range (e.g., 200-500 ms) for observing a deflection or a feature of the deflection representing the ERP-Pe component, (2) an expected direction of the deflection (e.g., positive) relative to a baseline, (3) an expected magnitude range of the deflection, (4) an expected location relative to the head of the human subject (e.g., an expected EEG interface by which the deflection in electrical potential is observed, and/or (5) presence of a previously observed ERP-Ne component within a time-locked EEG signal. As described in further detail with reference to FIGS. 4 and 5, this Pe-characteristic fluctuation in electrical potential may be used to detect whether an ERP-Pe component is present within an EEG signal.

The timeline of FIG. 3A depicts how the ERP-Ne component, which is indicative of a stimulus event containing an error or anomaly, typically occurs prior to the ERP-Pe component of the same ERP, which is indicative of the human subject's recognition of that error or anomaly. In scenarios where the human subject does not recognize the error or anomaly, the ERP-Pe will not be observed. Detection of an ERP-Ne component without detecting a subsequent ERP-Pe component for the same ERP may be used within the context of an HMD device to programmatically notify the user or other users (e.g., supervisors) of the need to take corrective action with respect to the erroneous or anomalous action performed by the user, or an erroneous or anomalous event perceived by the user. Furthermore, detection of an ERP-Ne component without detecting a subsequent ERP-Pe component for that same ERP or without the user taking corrective action to remedy the error or anomaly may be used to programmatically update a user profile of that user or a task profile of an applicable task to take corrective action with respect to the user (e.g., additional training or the need for rest) and/or to enable other users (e.g., supervisors or co-workers) to take corrective action with respect to the erroneous or anomalous action or event.

Detection of an ERP-Ne component accompanied by subsequent detection an ERP-Pe component for that same ERP may be used within the context of an HMD device to programmatically undo the previous action performed by the user (e.g., selections performed within a user interface of the HMD device) and/or present user interface elements (e.g., via a graphical display of the HMD device) that enable the user to address the error or anomaly without manually requiring that user to summon or navigate to the user interface elements. Furthermore, detection of an ERP-Ne component with subsequent detection an ERP-Pe component for that same ERP without the user taking corrective action may be used to programmatically update a user profile of that user or a task profile of the applicable task to enable other users (e.g., supervisors) to take corrective action (e.g., disciplinary action) with respect to the user as well as with respect to the erroneous or anomalous action.

Figure 3B:
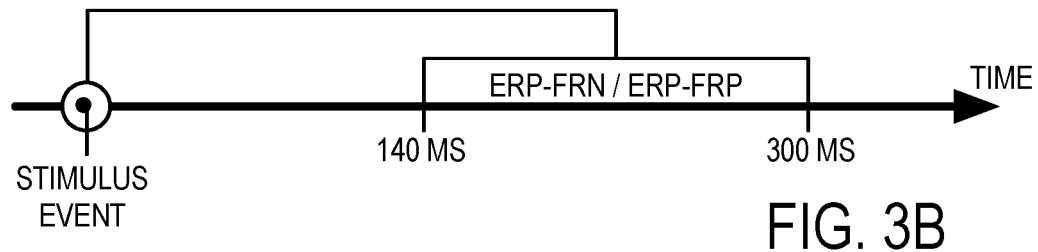
FIG. 3B is a timeline depicting an example relationship between a stimulus event and resulting fluctuations in electrical potential indicative of an ERP, including a feedback-related negativity (ERP-FRN) component or a feedback-related positivity (ERP-FRP) component observed via one or more EEG interface(s).

FIG. 3B is a timeline depicting an example relationship between a stimulus event and resulting fluctuations in electrical potential indicative of an ERP, including a feedback-related negativity (ERP-FRN) component or a feedback-related positivity (ERP-FRP) component observed via one or more EEG interface(s).

An ERP-FRN may be elicited by providing a human subject with a stimulus in the form of a visual, aural, or haptic feedback indicating a negative result (e.g., an error or anomaly, unexpected result, or other negative commentary) with respect to an action performed by that human subject. The ERP-FRN component typically occurs in response to a humans subject receiving feedback (e.g., a visual or auditory stimulus) indicating that the subject's performance is worse than expected in a given context. If the stimulus instead indicates a positive or expected result (e.g., a correct action or confirmatory commentary) with respect to the action performed by the human subject, an ERP-FRP may be instead elicited and observed via one or more EEG interfaces.

As depicted in FIG. 3B, the ERP-FRN or ERP-FRP component of the ERP may be observed approximately 140-300 ms following onset of a stimulus that indicates either an error or anomaly, or a correct or expected result. This 140-300 ms time period may be referred to as an ERP-FRN/ERP-FRP search window. It will be appreciated that this time range represents an example time range for ERP-FRN or ERP-FRP, as various operating conditions (described above with reference to ERP-Ne) may influence the timing of fluctuations in electrical potential indicative of these ERP components.

The ERP-FRN component typically presents as a negative deflection in electrical potential relative to a baseline. Whereas, the ERP-FRP component typically presents as a positive deflection in electrical potential relative to a baseline. The ERP-FRN and ERP-FRP components may be observed via at least one electrode of an EEG interface that is located at or near a fronto-central (e.g., Fz) location relative to the head of the human subject. However, other suitable locations (e.g., right or left of the midline and/or forward or rearward of Fz location) may be used to observe the ERP-FRP or ERP-FRN components.

A FRN-characteristic fluctuation in electrical potential may be collectively defined by one or more of the following: (1) an expected time range (e.g., 140-300 ms) for observing a deflection representing the ERP-FRN component, (2) an expected direction of the deflection (e.g., in a negative voltage direction) relative to a baseline, (3) an expected magnitude range of the deflection, and/or (4) an expected location relative to the head of the human subject (e.g., an expected EEG interface) by which the deflection in electrical potential is observed. A FRN-characteristic fluctuation in electrical potential may be collectively defined by one or more of the following: (1) an expected time range (e.g., 140-300 ms) for observing a deflection representing the ERP-FRN component, (2) an expected direction of the deflection (e.g., in a positive voltage direction) relative to a baseline, (3) an expected magnitude range of the deflection, and/or (4) an expected location relative to the head of the human subject (e.g., an expected EEG interface) by which the deflection in electrical potential is observed.

Within the context of an HMD device, detecting ERP-FRN or ERP-FRP components may be used to infer whether a user input included an error or anomaly, or was correctly provided by the user. Upon detecting an ERP-FRN component, the HMD device may present one or more user interface elements that enable the user to change or remedy the erroneous or anomalous user input. Upon detecting an ERP-FRP component, the HMD device or HMD system may validate a user input as the user input which was intended by the user (e.g., pass the user input to a process for execution by a computing device), thereby enabling the HMD device or HMD system to programmatically move on to subsequent task.

Figure 3C:
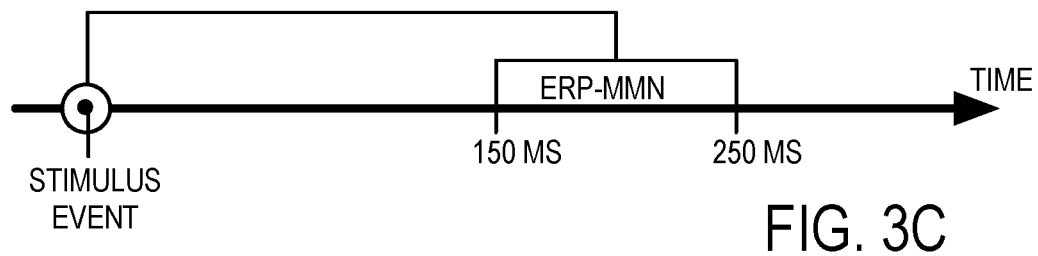
FIG. 3C is a timeline depicting an example relationship between a stimulus event and resulting fluctuations in electrical potential indicative of an ERP, including a mismatch negativity (ERP-MMN) component observed via one or more EEG interface(s).

FIG. 3C is a timeline depicting an example relationship between a stimulus event and resulting fluctuations in electrical potential indicative of an ERP, including a mismatch negativity (ERP-MMN) component observed via one or more EEG interface(s).

In this example, the stimulus event refers a human subject perceiving a sequence of baseline stimuli having oddball stimuli interspersed within the sequence. The sequence of stimuli may include a many-to-one ratio of baseline stimuli to at least one oddball stimulus for eliciting an ERP-MMN component. For example, a repeating sequence of baseline stimuli may be presented to the human subject with the oddball stimulus presented among or following the baseline stimuli. The ERP-MMN is typically considered to be an automatic human response. For example, the ERP-MMN component may be observed via one or more EEG interfaces whether or not the human subject is paying attention to the baseline or oddball stimuli.

As depicted in FIG. 3C, the ERP-MMN reaches its maximum deflection from the baseline approximately 150-250 ms after an oddball stimulus is presented to the human subject. It will be appreciated that this time range represents an example time range for ERP-MMN, as various operating conditions (described above with reference to ERP-Ne) may influence the timing of fluctuations in electrical potential indicative of these ERP components. Furthermore, for the ERP-MMN component, the latency may decrease with the increasing magnitude of stimulus change (e.g., difference in perceivable features between the baseline and oddball stimuli) between the oddball stimulus and the baseline stimuli. As will be described in further detail with reference to FIG. 7A, the ERP-MMN component may be used to determine a skill level (a level of experience) of a human subject with respect to a particular task.

Figure 3D:
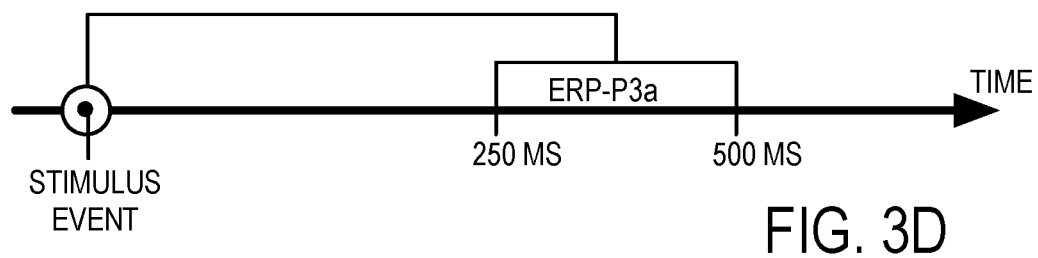
FIG. 3D is a timeline depicting an example relationship between a stimulus event and resulting fluctuations in electrical potential indicative of an ERP, including a novelty P3 or P3a (ERP-P3a) component observed via one or more EEG interface(s).

FIG. 3D is a timeline depicting an example relationship between a stimulus event and resulting fluctuations in electrical potential indicative of an ERP, including a novelty-P3 or P3a (ERP-P3a) component observed via one or more EEG interface(s). The ERP-P3a component may be produced by an infrequent distinct stimulus presented in a series of frequently encountered stimuli. The ERP-P3a component is referred to as a passive response, which does not require that the human subject attend to the stimulus.

The ERP-P3a component is characterized as a positive deflection in electrical potential relative to a baseline that is typically observed within a time period 250-500 ms subsequent to onset of a stimulus event. For example, this positive deflection may be up to 20.0 microvolts at the maximum peak within the time period as compared to a pre-stimulus baseline voltage. Typically, the P3a component has a central/parietal maximum amplitude distribution and relatively short peak latency. These aspects of the ERP-P3a component may be referred to as the P3a-characteristic fluctuation in electrical potential.

Following detection of a waveform that exhibits an ERP component characteristic deflection within a typical ERP search window, a waveform profile may be established in a database system that represents an association between or among a variety of information relating to the waveform event. As a non-limiting example, an association may be established between some or all of the following information with regards to a detected ERP waveform: (1) a waveform event identifier that is sufficiently unique within a domain to enable a particular instance of a detected ERP waveform to be distinguished from other instances of detected ERP waveforms with respect to the human subject and/or among other human subjects of a group, (2) sampling data obtained from the EEG signal representing the waveform and/or data surrounding the waveform within a buffer region (e.g., voltage values vs. time values describing the waveform), (3) baseline data obtained from the EEG signal representing a baseline voltage prior to onset of the stimulus and/or between onset of the stimulus and the beginning of the waveform deflection, (4) a peak-amplitude value (e.g., maximum voltage value) at the peak of the waveform (e.g., measured relative to the baseline or other reference value), (5) a peak-time value at the peak of the waveform (e.g., measured relative to the onset of stimulus event) or other suitable measure of latency of the waveform in relation to onset of the stimulus event, (6) a trial number for the stimulus event within a set of stimulus events presented to the human subject during the current session for eliciting the ERP component and/or across all sessions for the human subject, (7) a wavelength or time-based measurement of the waveform within the time domain, (8) an average magnitude or integral of the waveform, (9) a measurement of the degree of symmetry of the waveform about the peak-amplitude value within the voltage and/or time domains, among other suitable data. A waveform of an ERP component may be characterized based on some or all of the above data items that may be associated with the waveform profile, enabling specific ERP component types to be identified within EEG signals.

Figure 4:
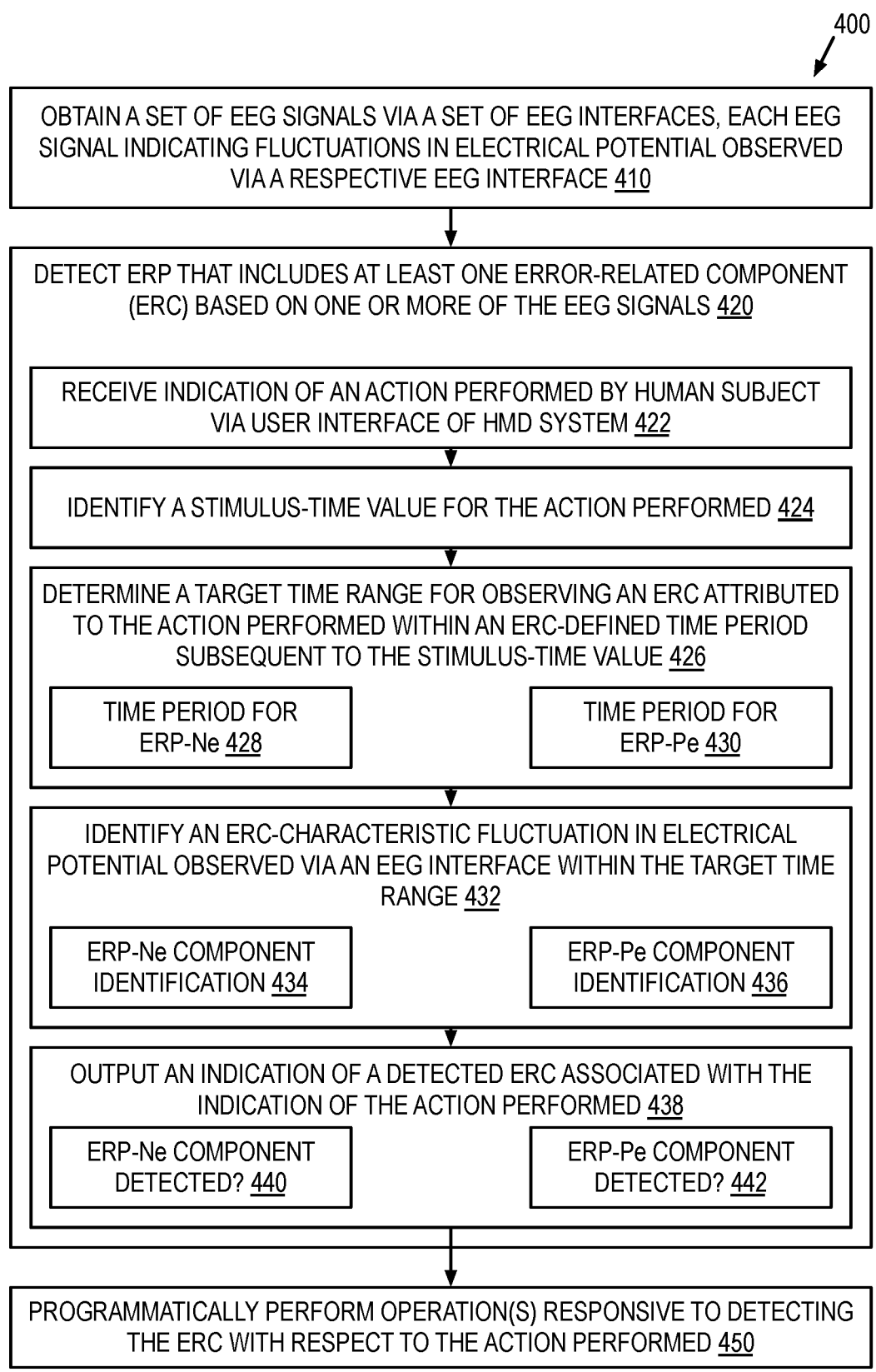
FIGS. 4 and 5 are flow diagrams depicting example methods associated with detecting ERP components, including an error-related negativity (ERP-Ne) component and an error-related positivity (ERP-Pe) component.
Figure 5:
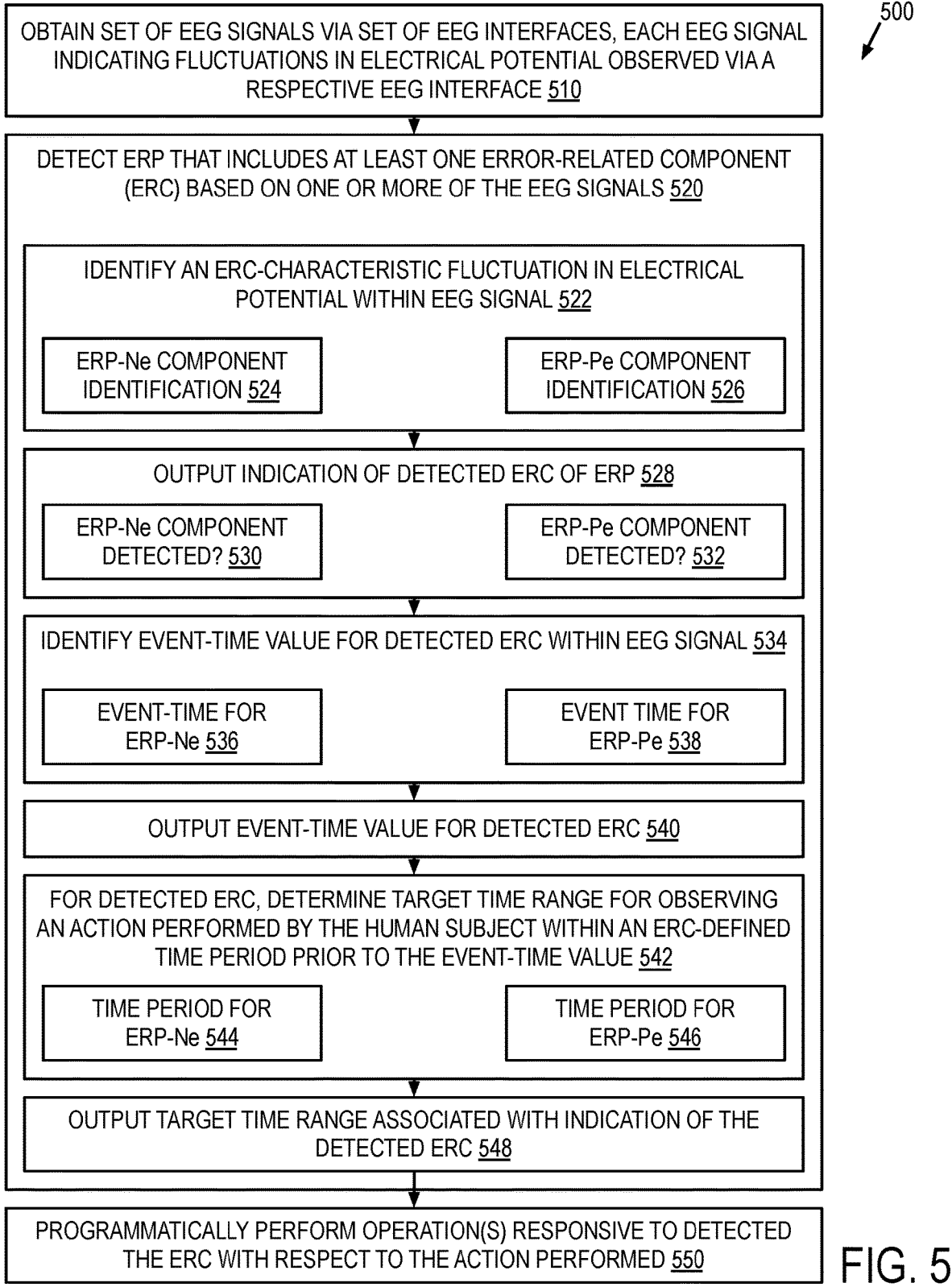

FIGS. 4 and 5 are flow diagrams depicting example methods associated with detecting ERP components, including an error-related negativity (ERP-Ne) component and an error-related positivity (ERP-Pe) component. ERP-Ne and ERP-Pe components may each be referred to as an error-related component (ERC) of an ERP. Such error-related components may be observed following a human subject perceiving a stimulus event, such as the human subject performing an activity that includes an error or anomaly, or observing an event that includes an error or anomaly.

Method 400 of FIG. 4 may be used to determine a target time range within which ERP-Ne or ERP-Pe components may be observed or otherwise identified following a stimulus event. By contrast, method 500 of FIG. 5 may be used to determine a target time range within which stimulus event may be identified prior to observing ERP-Ne and/or ERP-Pe components.

In some implementations, methods 400, 500 or portions thereof may be performed by a computing device located on-board an HMD device, while in other implementations, portions of methods 400, 500 may be performed off-board the HMD device by one or more off-board computing devices. Methods 400 and 500 may be performed in combination with each other in some implementations to achieve robust matching between stimulus events and observed ERP components.

Referring to method 400 of FIG. 4, the method at 410 includes obtaining a set of one or more EEG signals via a set of one or more EEG interfaces, respectively. The set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, and storing or otherwise buffering the signal information in a data storage device. In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 420, the method includes detecting an event-related potential (ERP) event that includes at least one error-related component (ERC) based on one or more of the EEG signals of the set of EEG signals. Within the context of the present disclosure, an ERC may refer to either an error-related negativity (ERP-Ne) component or an error-related positivity (ERP-Pe) component of the ERP. Detecting an ERP that includes at least one ERC at 420 may be achieved by further performing one or more of operations 422-442 that form sub-processes of operation 420.

Figure 8:
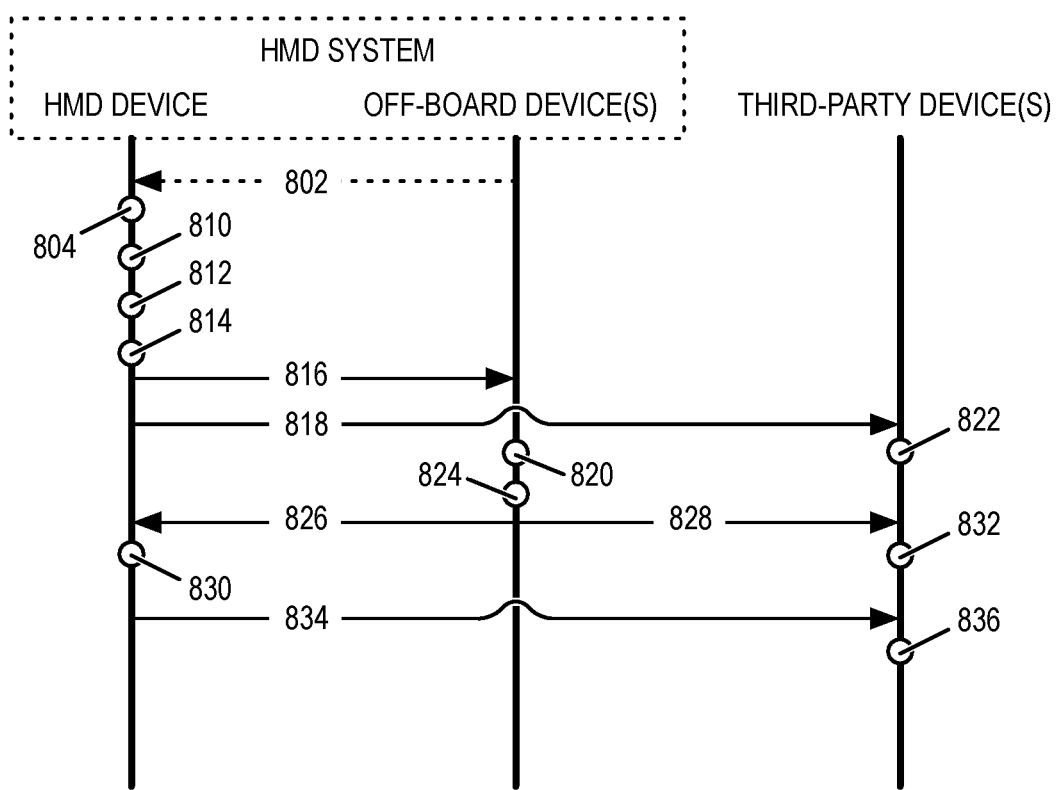
FIG. 8 is a diagram depicting example interactions between an HMD device, off-board device(s) of an HMD system, and third-party device(s) that are external the HMD system.

At 422, the method includes receiving an indication of an action performed by the human subject via a user interface of the HMD system. This action may serve as a stimulus event that elicits an ERP from the human subject. For example, the action may include the user making a selection between two or more options by providing a user input to the HMD device or HMD system. The user interface may form part of the HMD device or may form part of an off-board device (e.g., peripheral device, sensor device, etc.) of an HMD system that interfaces with the HMD system. Alternatively, the method at 422 may include receiving an indication of an event that is perceived or perceivable by the user instead of an action. This event may also serve as a stimulus event that elicits an ERP from the human subject. The indication of an event may be received as a sensor measurement of an environmental condition via a sensor device of the HMD device or HMD system. As another example, the event may exist and be perceived within an augmented or mixed reality view provided by a graphical display of the HMD device or other peripheral. FIG. 8 depicts example interactions between an HMD device and off-board devices of an HMD system.

At 424, the method includes identifying a stimulus-time value for the stimulus event, such as an action performed by the human subject or an event perceived/perceivable by the human subject). For example, where the action refers to a user input provided by the human subject via a user interface. A time that the user input was received via the user interface may be set as the stimulus-time value for the action performed by the human subject. Where the stimulus event is an event that is perceivable or perceived by the user, the stimulus-time value may be identified based on time stamps or other time values assigned to sensor data that records the event. Where the event is perceived or perceivable within an augmented or mixed reality view presented by the HMD device, the stimulus-time value may be identified as the time at which the event was presented to the human subject.

At 426, the method includes determining a target time range for observing an ERC attributed to the action performed within an ERC-defined time period subsequent to the stimulus-time value. As a first example, at 428, a first time period for detecting an ERP-Ne component refers to an Ne-defined time period of 80-150 milliseconds subsequent to the stimulus-time value. As a second example, at 430, a second time period for detecting an ERP-Pe component refers to a Pe-defined time period of 200-500 milliseconds subsequent to the stimulus-time value. Again, it will be understood that these example time ranges may vary based on operating conditions as previously described with reference to FIG. 3A. The Ne-defined time period may refer to the previously described ERP-Ne search window and the Pe-defined time period may refer to the previously described ERP-Pe search window of FIG. 3A.

At 432, the method includes identifying an ERC-characteristic fluctuation in electrical potential observed via an EEG interface within the target time range. As a first example, at 434, identifying the ERC-characteristic fluctuation includes identifying an Ne-characteristic fluctuation in the electrical potential observed via an EEG interface. This EEG interface may, for example, be located at or near a frontal location (e.g., Fp) or a fronto-central location (e.g., Fz) relative to the head of the human subject. As a second example, at 436, identifying the ERC-characteristic fluctuation includes identifying a Pe-characteristic fluctuation in the electrical potential observed via an EEG interface located at or near a central location (e.g., Cz) or a parietal location (e.g., Pz) relative to the head of the human subject. However, other suitable electrode locations may be used to identify ERP-Ne and ERP-Pe components, such as previously described with reference to FIG. 3A.

At 438, the method includes outputting an indication of a detected ERC associated with the indication of the stimulus event (e.g., action or event). Operation 438 may be performed responsive to identifying the ERC-characteristic fluctuation within the target time range at 432. As sub-processes to operation 438, at 440, it may be determined whether an ERP-Ne component was detected, and at 442, it may be determined whether an ERP-Pe component was detected. In some implementations, outputting the indication of the detected ERC includes outputting a stimulus to the human subject via an output device of the HMD system. This stimulus may provide feedback to the user regarding the detected ERC. Operations 440 and 442 may be performed in series or in parallel to enable detection of an ERP-Ne followed by an ERP-Pe as components of the same ERP.

With regards to ERP-Ne detection, the stimulus may represent the error or anomaly in the action performed by the human subject. The stimulus output by the HMD device may include one or more of a visual, aural, and/or haptic stimulus. For example, outputting an indication of a detected ERP-Ne component may include outputting an indication of an error or anomaly being associated with the action or event for presentation via the near-eye graphical display device. As another example, outputting an indication of a detected ERP-Pe component may include outputting a user interface element that enables the human subject to correct or log an error or anomaly in the action performed by the human subject or the perceived event. For implementations in which the HMD system includes off-board devices, outputting the indication of the detected ERC may include transmitting the indication of the detected ERC from the on-board computing device to the off-board computing device over a wireless communications network, for example. These operations may be programmatically performed by the HMD device or HMD system responsive to detection of an ERP-Ne or ERP-Pe.

A magnitude of deflection in the fluctuations in electrical potential for an ERP-Ne component may vary with task difficulty. Specifically, obvious errors or anomalies in a stimulus event will typically elicit a stronger (e.g., larger magnitude deflection) for the ERP-Ne component. Accordingly, in some implementations, a magnitude of deflection for ERP-Ne events may be output by the HMD device or HMD system, and may transmitted to other devices and/or stored for reference. This magnitude of deflection may be used by the HMD device or HMD system to programmatically perform one or more operations that vary in response to the magnitude.

At 450, the method includes programmatically performing one or more operation(s) responsive to the detected ERP-Ne component or ERP-Pe component with respect to the stimulus event, such as the action performed by the human subject or the event perceived by the human subject. Examples of such operations are further described with reference to FIG. 8.

Referring to method 500 of FIG. 5, the method at 510 includes obtaining a set of one or more EEG signals via a set of one or more EEG interfaces, respectively. As previously described with reference to method 400, the set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, and storing or otherwise buffering the signal information in a data storage device. In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 520, the method includes detecting an ERP that includes at least one error-related component (ERC) based on one or more of the EEG signals of the set of EEG signals. As previously described with reference to method 400 of FIG. 4, an ERC may refer to either an ERP-Ne component or an ERP-Pe component of the ERP. Detecting an ERP that includes at least one ERC at 520 may be achieved by further performing one or more of operations 522-548 that form sub-processes of operation 520.

At 522, identifying an ERC-characteristic fluctuation in the electrical potential within the set of EEG signals. For example, for each of the one or more EEG signals, an ERC-characteristic fluctuation in the electrical potential may be identified within that EEG signal. As a first example, at 524, identifying the ERC-characteristic fluctuation includes identifying an Ne-characteristic fluctuation in the electrical potential observed via an EEG interface located at or near a frontal location (e.g., Fp) or a fronto-central location (e.g., Fz) relative to the head of the human subject. As a second example, at 526, identifying the ERC-characteristic fluctuation includes identifying a Pe-characteristic fluctuation in the electrical potential observed via an EEG interface located at or near a central location (e.g., Cz) or a parietal location (e.g., Pz) relative to the head of the human subject. However, other suitable locations may be used to observe the ERP-Ne and ERP-Pe components, as previously described with reference to FIG. 3A.

At 528, the method includes outputting an indication of a detected ERC and an event-time value for the detected ERC. Operation 528 may be performed responsive to identifying the ERC-characteristic fluctuation. For example, at 530, it may be determined whether an ERP-Ne component was detected, and at 532, it may be determined whether an ERP-Pe component was detected.

At 534, the method includes, identifying an event-time value for each detected ERC within the EEG signal. As a first example, at 536, a first event-time value for the ERP-Ne component (if present) may be identified. As a second example, at 538, a second event-time value for the ERP-Pe component (if present) may be identified. At 540, the method includes outputting the event-time value for the detected ERC, which may include outputting first and second event-time values for ERP-Ne and ERP-Pe components (if present). Depending on waveform detection techniques or implementation, the event-time value may correspond to a particular feature of the deflecting waveform for the ERP component. For example, the event-time value may correspond to a peak of deflection, a beginning of the deflection, a threshold deflection from a baseline, an end of the deflection, etc.

At 542, the method includes, for each detected ERC, determining a target time range for observing a stimulus event, such as an action performed by the human subject (or an event perceived/perceivable by the human subject) within an ERC-defined time period prior to the event-time value. As a first example, at 544, the ERC-defined time period refers to an Ne-defined time period of 80-150 milliseconds prior to the event-time value associated with the Ne-characteristic fluctuation. As a second example, at 546, the ERC-defined time period refers to a Pe-defined time period of 200-500 milliseconds prior to the event-time value associated with the Pe-characteristic fluctuation. This target time range may be referred to as a stimulus event search window within which a stimulus event may be identified that is likely to have elicited the ERP components.

At 548, the method includes outputting a target time range associated with the indication of the detected ERC. In some implementations, method 500 may further include identifying a target stimulus event (e.g., action or event) from among a set of observed stimulus events based on the target time range associated with the indication of the detected ERC. An indication of the target stimulus event may be output by the HMD system. For example, an indication of a target action or event (as examples of a stimulus event) may be presented via the near-eye graphical display device, or other suitable stimulus may be output by the HMD device or HMD system, such as auditory or haptic stimulus. As another example, an indication of the target action or event may be output by transmitting the indication of the target action or event from the on-board computing device to an off-board computing device (e.g., an off-board device of the HMD system or a third-party device) over a wireless or wired communications network.

At 550, the method includes programmatically performing one or more operation(s) responsive to the detected ERP-Ne component and/or ERP-Pe component with respect to the action performed by the human subject. Examples of such operations are further described with reference to FIG. 8.

Figure 6:
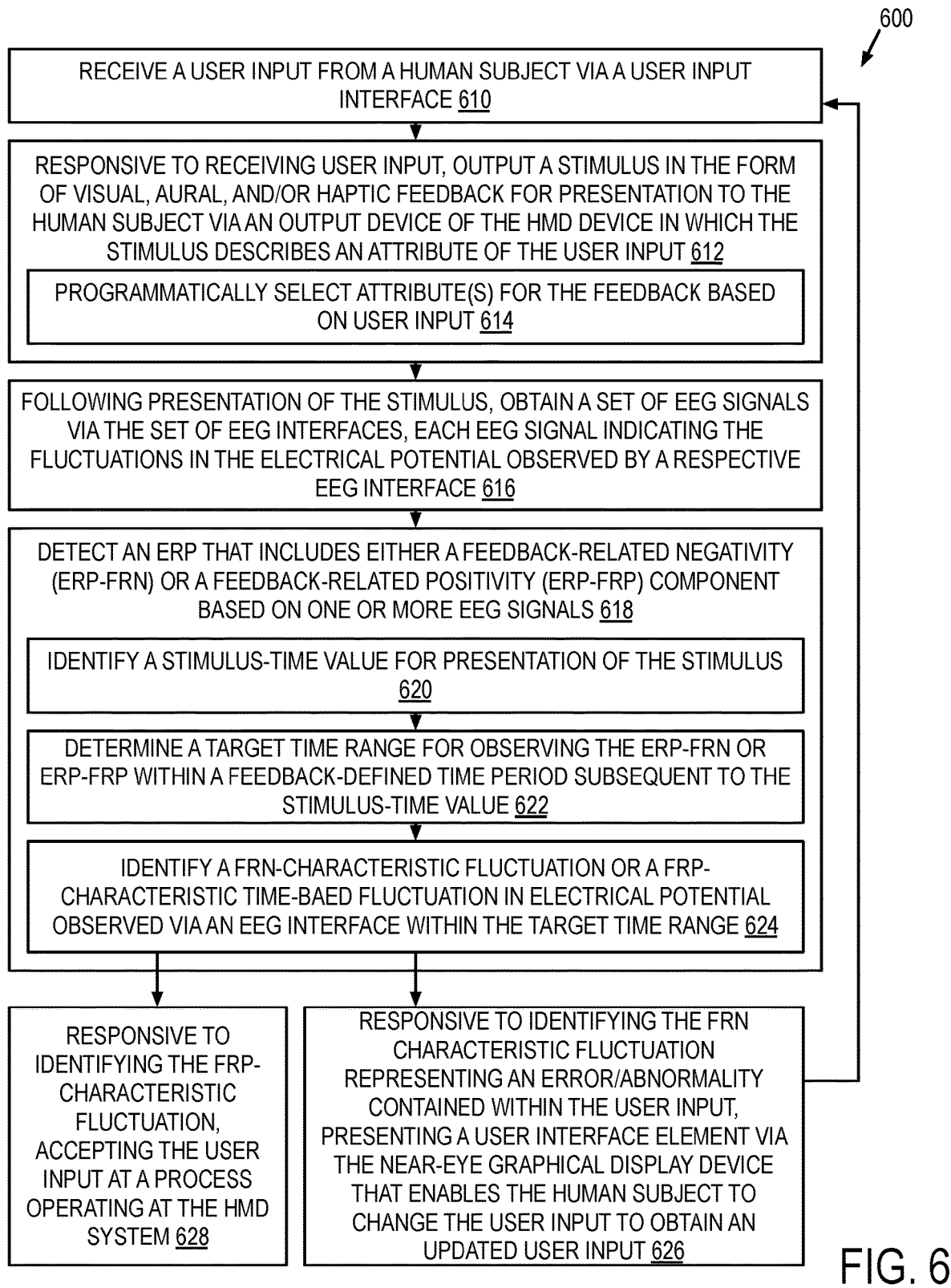
FIG. 6 is a flow diagram depicting an example method associated with detecting ERP components, including a feedback-related negativity (ERP-FRN) component and a feedback-related positivity (ERP-FRP) component.

FIG. 6 is a flow diagram depicting an example method 600 associated with detecting ERP components, including a feedback-related negativity (ERP-FRN) component and a feedback-related positivity (ERP-FRP) component. In some implementations, method 600 or portions thereof may be performed by a computing device located on-board an HMD device, while in other implementations, portions of method 600 may be performed off-board the HMD device by one or more off-board computing devices. Method 600 may be performed in combination with methods 400 and/or 500 in some implementations to achieve robust matching between stimulus events and observed ERP components.

At 610, the method includes receiving a user input from the human subject via a user input interface of the HMD system. The user input may be received via a user input interface of the HMD device or via an off-board device of the HMD system. The user input may refer to an action performed by the human subject, such as selecting a graphical icon presented via the HMD device or interacting with real-world objects that may be detected by a sensor device. This sensor device may form part of the HMD system or may interface with the HMD system via a wired or wireless communications network.

At 612, the method includes responsive to receiving the user input, outputting a stimulus for presentation to the human subject via an output device of the HMD device. The stimulus may take the form of visual, aural, and/or haptic feedback. The stimulus describes one or more attribute(s) of the user input to enable the human subject to determine whether the user input that was received by the HMD system was the user input that was intended by the human subject. In some implementations, a computing device of the HMD device or HMD system may determine whether the user input contained an error or may score the user input according to a pre-defined scoring system. In this implementation, the feedback provided by the stimulus may be selected to identify or indicate the user input contained an error or anomaly, or may indicate the score identified by the computing device. In other implementations, the feedback may indicate a feature of the user input, such as the content of the user input or a selection indicated by the user input, without determining whether the user input contains an error or anomaly. Here, the feedback provided to the user enables the user to perceive the user input that has been received by the HMD device or HMD system, and judge whether the user input contained an error or anomaly. As a sub-process of operation 612, at 614, the method may include programmatically selecting the attribute(s) for the feedback based on the user input. For example, the modality of the user input may be used to determine which attributes of the user input are presented to the user. Selection of graphical icons, for example, may include feedback that entails visual stimulus within the graphical display of the HMD device. As another example, selection of a physical button or graphical icon may include feedback that entails auditory and/or haptic stimulus.

Following presentation of the stimulus, at 616, the method includes obtaining a set of one or more EEG signals via a set of one or more EEG interfaces, respectively. The set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, and storing or otherwise buffering the signal information in a data storage device. In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 618, the method includes detecting an ERP that includes either a feedback-related negativity (ERP-FRN) component or a feedback-related positivity (ERP-FRP) component based on one or more of the EEG signals. Detecting an ERP that includes an ERP-FRN or ERP-FRP component at 618 may be achieved by further performing one or more of operations 620-624 that form sub-processes of operation 618.

At 620, the method includes identifying a stimulus-time value for the presentation of the stimulus. For example, a time that the stimulus was presented to the human subject at 612 and capable of being perceived by the human subject may be set as the stimulus-time value. The stimulus-time value may be stored in a data storage device from which it may be referenced.

At 622, the method includes determining a target time range for observing the ERP-FRN or ERP-FRP within a feedback-defined time period subsequent to the stimulus-time value. As previously described with reference to FIG. 3B, a feedback-defined time period may correspond to approximately 140-300 milliseconds after presentation of the stimulus to the human subject. It will be appreciated that this time range represents an example time range. In real-world implementations, the time range for observing the ERP-FRP or ERP-FRN components may vary with operating conditions, as previously described with reference to FIGS. 3A, 3B, 3C, and 3D.

At 624, the method includes identifying a FRN-characteristic fluctuation or a FRP-characteristic fluctuation in electrical potential observed via an EEG interface within the target time range. The FRN-characteristic or FRP-characteristic fluctuations in electrical potential may be observed via an EEG interface that is located at or near a fronto-central (e.g., Fz) location relative to the head of the human subject. However, other suitable locations may be used to observe the ERP-FRP or ERP-FRN components.

At 626, the method includes responsive to identifying the FRN-characteristic fluctuation representing an error or anomaly contained within the user input, presenting a user interface element via the near-eye graphical display device that enables the human subject to change the user input to obtain an updated user input via the user input interface. This updated user input may replace or augment the previous user input that contained an error or anomaly that elicited the ERP-FRN component. In some implementations, method 600 may be repeated for the updated user input received from the human subject by returning to operation 610.

At 628, the method includes responsive to identifying the FRP-characteristic fluctuation, accepting the user input at a process operating at the HMD device or HMD system. For example, the user input may be used by a program operating at an on-board computing device of the HMD device or at an off-board computing device of the HMD system to effect a change of state of that program.

In some implementations, method 600 may further include transmitting an indication of a detected ERP-FRN or a detected ERP-FRP from the HMD device to an off-board computing device (e.g., an off-board device of the HMD system or a third-party device) over a wireless or wired communications network. The HMD device or HMD system may programmatically perform one or more operations responsive to detecting an ERP-FRN or an ERP-FRP component. Examples of such operations are further described with reference to FIG. 8.

Figure 7A:
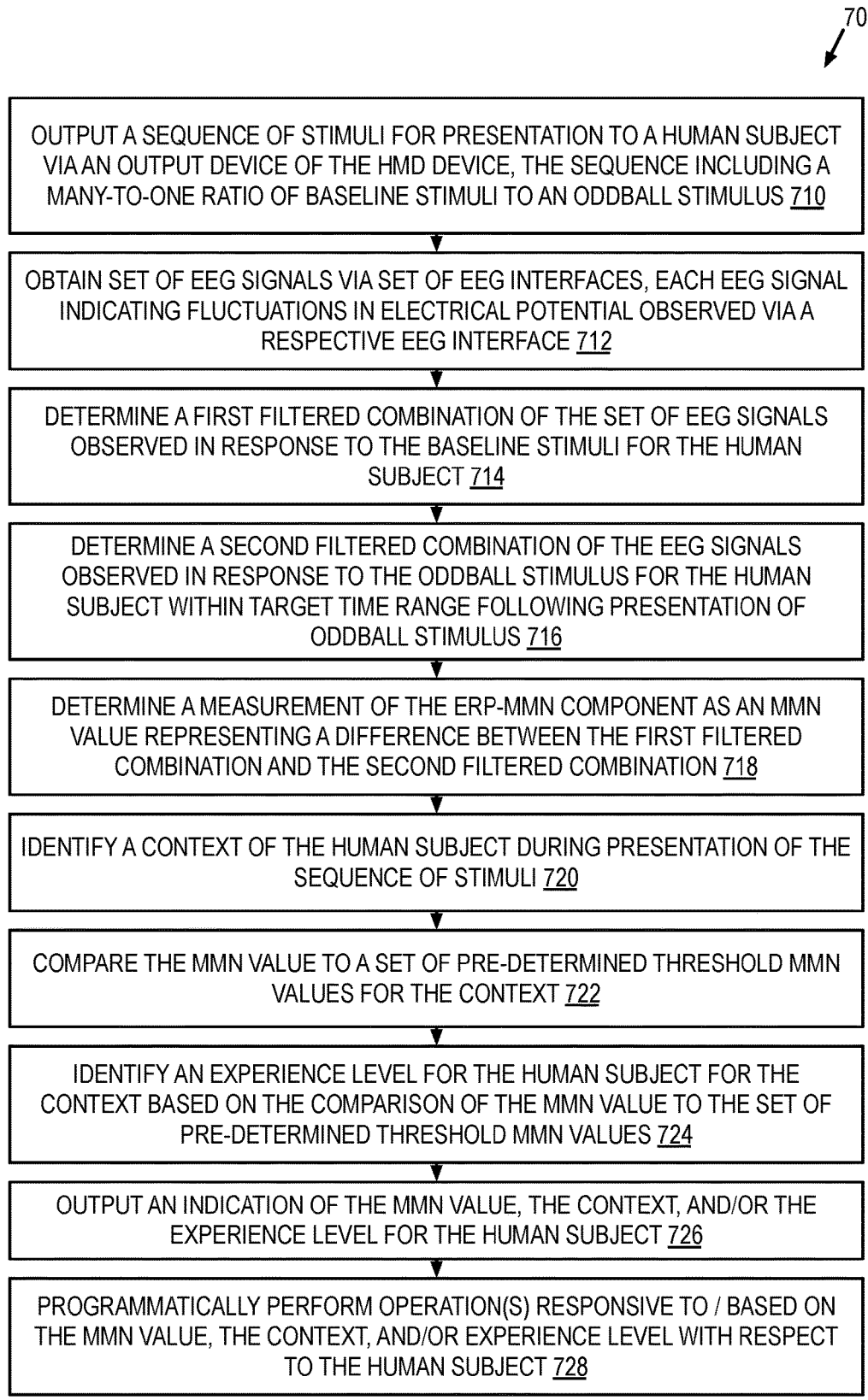
FIG. 7A is a flow diagram depicting an example method associated with detecting ERP components, including a mismatch negativity (ERP-MMN) component.

FIG. 7A is a flow diagram depicting an example method 700 associated with detecting ERP components, including a mismatch negativity (ERP-MMN) component. Detecting an ERP-MMN component may enable automated classification of a human subject as expert or novice with respect to a particular task. Knowledge of a person's skill level with respect to a particular task may inform whether additional training should be assigned to that person or whether additional instructions should be provided to that person to enable correct performance and completion of the task. In some implementations, method 700 or portions thereof may be performed by a computing device located on-board an HMD device, while in other implementations, portions of method 700 may be performed off-board the HMD device by one or more off-board computing devices.

At 710, the method includes outputting a sequence of stimuli for presentation to a human subject. The stimuli may include visual, aural, and/or haptic stimuli that is presented by the HMD device. The sequence of stimuli may include a many-to-one ratio of baseline stimuli to at least one oddball stimulus for eliciting an ERP-MMN component. For example, a repeating sequence of baseline stimuli may be presented to the human subject with the oddball stimulus presented among or following the baseline stimuli. This sequence of baseline and oddball stimuli may be repeated one or more times, and/or may be combined with one or more other sequences containing a many-to-one ratio of baseline stimuli to an oddball stimulus for eliciting an EPR-MMN component, thereby providing a longer sequence having two or more oddball stimuli interspersed among baseline stimuli.

At 712, the method includes obtaining a set of one or more EEG signals via a set of one or more EEG interfaces. The set of EEG interfaces may include a plurality of spatially distributed electrodes that are mounted to an HMD device or other suitable EEG device that is wearable by a human subject. Each EEG signal of the set of EEG signals may indicate fluctuations in the electrical potential measured via a respective EEG interface that observe a respective location relative to a head of a human subject. The EEG signals may be time-locked with each other to enable comparison of their respective fluctuations between or among each other at particular points in time. The EEG signals may be time-locked to a stimulus event to enable fluctuations in the EEG signals to be attributed to a response by the human subject to perceiving the stimulus event. A computing device located on-board the HMD device may obtain the set of EEG signals by receiving, sampling, and storing or otherwise buffering the signal information in a data storage device (e.g., as sampled data). In some implementations, the computing device may assign time-stamps or other time indicators to predefined locations within each EEG signal to enable time-locking of the signals. The computing device may implement a time-locking operation between or among the EEG signals by aligning the time-stamps or other time indicators to obtain a set of time-locked EEG signals. In some implementations the set of EEG signals may initially take the form of one or more analog signals that are converted at the HMD device to one or more digital signals for further processing and/or storage.

At 714, the method includes determining a first filtered combination of the set of EEG signals that represent a response by a human subject to perceiving the baseline stimuli over multiple trials or exposures to interspersed oddball stimulus. The first filtered combination may include an average of multiple time-locked electrical potentials of the EEG signals, with each EEG signal representing a response by the human subject to perceiving the baseline stimuli.

At 716, the method includes determining a second filtered combination of the set of EEG signals that represent a response by the human subject to perceiving the oddball stimulus over multiple trials or exposures to the oddball stimulus. The second filtered combination may be the same type of filtered combination as the first filtered combination applied to EEG signals representing the subject's response to the baseline stimuli. For example, the second filtered combination include an average of multiple time-locked electrical potentials of the EEG signals representing a response by the human subject to perceiving the oddball stimulus.

At 718, the method includes determining a measurement of the ERP-MMN component as an MMN value representing a difference between the first filtered combination obtained at 714 and the second filtered combination obtained at 716. This MMN value (representing the difference) is typically a negative voltage value between −0.01 and −5.00 microvolts. However, this range may vary based on operating conditions. People having greater experience or a greater skill level (e.g., experts) within a particular context typically have an MMN value of a greater magnitude as compared to people having lesser experience or a lesser skill level (e.g., novices) within the same context. Typically, as the magnitude of MMN value increases, the user's skill level with regards to the particular context (e.g., a task) also increases, thereby enabling users to be ranked or scored with respect to their skill level as indicated by their respective MMN value.

At 720, the method includes identifying a context of the human subject during presentation of the sequence of stimuli. For example, the context may include a task presently being performed by the human subject or a task that is to be performed by the human subject. In some implementations, a context of the human subject may be identified with respect to the real-world environment and/or with respect to a program being implemented by a computing device of the HMD device or HMD system. Geo-positioning and/or orientation information (e.g., in 6DOF space) for the HMD device/human subject may be used to identify the context of the human subject. Computer vision applied to physical objects within the real-world environment captured via forward/outward facing cameras of the HMD device may be used to identify the context of the human subject. User input provided by the human subject to the HMD device or HMD system may be used to identify the context of the human subject. For example, the human subject may manually indicate or select the context by providing a user input to the HMD device or HMD system. A state of a program operating at the HMD device or HMD system that the human subject is interacting with or has recently interacted with may also be used to identify the context of the human subject. Tasks may be associated with particular geo-positioning and/or orientations, physical objects recognizable by computer vision, and/or program states, enabling the HMD device or HMD system to identify the context with which the skill level of the human subject is to be assessed.

In some implementations, operation 720 may be performed before operation 710 to enable the sequence of stimuli to be selected or otherwise defined with respect to the particular context of the human subject. For example, a first context may be associated with a first predefined sequence of stimuli for eliciting ERP-MMN components indicating a skill level with respect to the first context, and a second context may be associated with a second predefined sequence of stimuli for eliciting ERP-MMN components indicating a skill level with respect to the second context.

At 722, the method includes comparing the MMN value to a set of pre-defined threshold MMN values for the context identified at 720. The set of pre-determined threshold MMN values may include one or more threshold MMN values that delineate two or more skill levels for that context. In at least some implementations, the set of pre-determined threshold MMN values may be obtained from a training phase or from observations across many users within the contexts for which skill level is to be measured.

At 724, the method includes identifying a skill level for the human subject for the context based on the comparison of the MMN value to the set of pre-determined threshold MMN values. Threshold MMN values may alternatively or additionally be calibrated with respect to a specific type of user, such as expert vs. novice sets of users. For example, the human subject may be identified as being an expert or a novice with respect to a particular task. Each threshold MMN value of the set may include a pair of values representing corresponding skill levels associated with MMN values located on either side of the threshold.

At 726, the method includes outputting an indication of the MMN value, an indication of the context, and/or an indication of a skill level for the human subject. At 728, the method includes programmatically performing one or more operations responsive to and/or based on the MMN value, context, and/or skill level with respect to the human subject. Examples of such operations are further described with reference to FIG. 8.

Figure 7B:
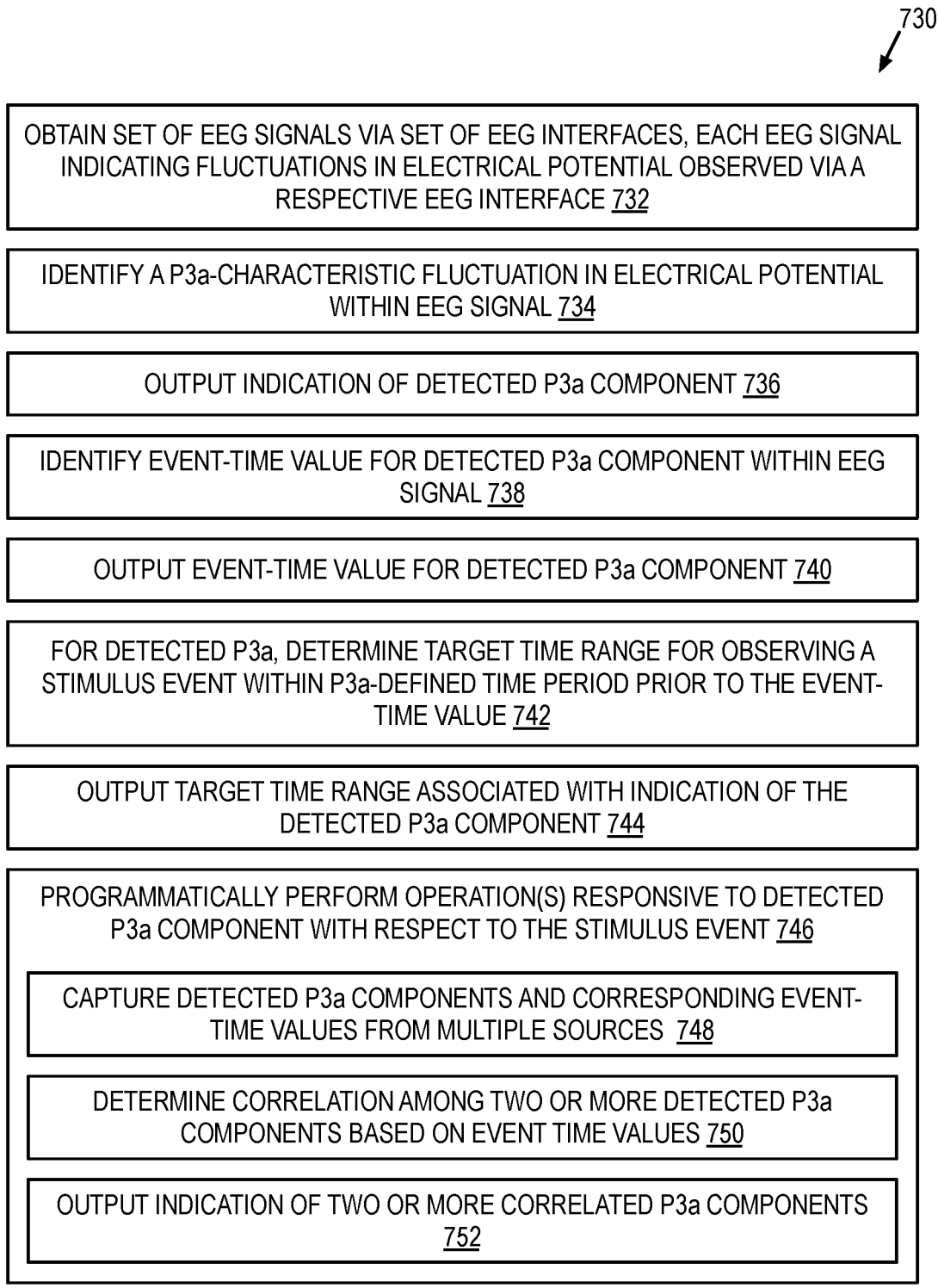
FIG. 7B is a flow diagram depicting an example method associated with detecting ERP components, including a novelty P3 or P3a (ERP-P3a) component.

FIG. 7B is a flow diagram depicting an example method 730 associated with detecting ERP components, including a novelty P3 or P3a (ERP-P3a) component. At 732, the method includes obtaining a set of EEG signals via a set of EEG interfaces. At 734, the method includes identifying a P3a-characteristic fluctuation in electrical potential within an EEG signal. At 736, the method includes outputting an indication of the detected P3a component. At 738, the method includes identifying an event-time value for the detected P3a component within the EEG signal. At 740, the method includes outputting an event-time value for the detected P3a component. At 742, the method includes for the detected P3a component, determining a target time range for observing a stimulus event within the P3a-defined time period prior to the event-time value. At 744, the method includes outputting the target time range associated with an indication of the detected P3a component. At 746, the method includes programmatically performing one or more operation(s) responsive to the detected P3a component with respect to the stimulus event. Operations 748, 750, and 752 may be sub-processes of operation 746. At 748, the method includes capturing the detected P3a components and corresponding event-time values from multiple sources (e.g., a plurality of HMD devices operated by respective users). At 750, the method includes determining a correlation (e.g., time-based proximity) among or between two or more detected P3a components based on the event time values obtained from the multiple sources. At 752, the method includes outputting an indication of the two or more correlated P3a components.

In at least some implementations, by continuously monitoring for ERP-P3a components within EEG signals, novel events that elicit an ERP-P3a component may be cross referenced against surrounding users (i.e., other users of HMD devices) to determine if multiple users concurrently generate ERP-P3a components. When multiple users demonstrate ERP-P3a component responses, the HMD system may capture audio and/or video of the stimulus event from multiple sources (e.g., the respective HMD devices of the users) or other audio/video capture devices. This captured data may be analyzed to determine whether an emergency condition or other unexpected issue requires attention within the general area of the users.

FIG. 8 is a diagram depicting example interactions between an HMD device, off-board device(s) that form part of an HMD system in combination with the HMD device, and third-party device(s) that are external the HMD system. Here, the HMD device, the off-board device(s), and the third-party device(s) of FIG. 8 are non-limiting examples of previously described HMD device 110, off-board device(s) 114, and third-party device(s) 140 of FIG. 1, respectively. The HMD system of FIG. 8 is a non-limiting example of previously described HMD system 112 of FIG. 1.

At 810, EEG signals may be obtained by the HMD device via a set of one or more EEG interfaces. The EEG signals may represent observations of the brain activity of a human subject, and may contain one or more ERPs. The ERPs may be generated in response to a stimulus event. In some examples, the stimulus event may result from a visual, auditory, and/or haptic stimulus output by the HMD device or HMD system, as indicated at 804. This stimulus may be generated on-board the HMD device or may be generated in response to a command communicated by off-board devices to the HMD device as indicated at 802. The HMD device may output a visual stimulus via a graphical display device of the HMD device or a peripheral device thereof, an auditory stimulus via an audio speaker of the HMD device or a peripheral device thereof, and/or a haptic stimulus via a haptic device of the HMD device or a peripheral device thereof.

At 812, the EEG signals may be processed at the HMD device to locally detect one or more ERP(s). At 814, the HMD device may programmatically perform one or more operations responsive to detecting the ERP(s). As an example of an operation that may be programmatically performed by the HMD device, at 816, the HMD device may communicate an indication of a detected ERP to one or more off-board device(s) that collectively form part of the HMD system. Alternatively or additionally, as indicated at 818, the HMD device may communicate an indication of the detected ERP to one or more third-party device(s) that reside outside of the HMD system. These communications may be transmitted and received over a communications network. An indication of a detected ERP may include or may be accompanied by event-associated information, as will be described in further detail below.

In at least some implementations, an indication of a detected ERP may include or take the form of an ERP identifier that identifies the specific instance of the detected ERP. This ERP identifier may include or may be based on a global time value of detection of the ERP, a user identifier for the human subject from which the ERP was observed, a hardware identifier for the HMD device by which the ERP was observed, a relative position of the ERP within a sequence of ERPs observed by the HMD device, etc. Furthermore, an identifier for each of the detected ERP components of the ERP may be included with or form part of the indication of the ERP. For example, an ERP may include ERP components such as ERP-Ne, ERP-Pe, ERP-FRN, ERP-FRP, ERP-MMN, etc. that were detected within the observed EEG signals. Each of these ERP components may be represented by a respective component identifier that enables multiple ERP components of an ERP to be identified and distinguished from each other based on their respective identifiers.

At 820, the off-board device(s) may receive the indication of the detected ERP(s) communicated by the HMD device at 816, and may programmatically perform one or more operations responsive to the indication. Alternatively or additionally, at 822, the third-party device(s) may receive the indication of the one or more ERPs communicated by the HMD device at 818, and may programmatically perform one or more operations responsive to the indication.

In another implementation, EEG signal information obtained at 810 may be instead communicated at 816 by the HMD device to the off-board device(s) for processing, as indicated at 816. The off-board device(s) may receive and process the EEG signal information to detect one or more ERP(s) at 820. At 824, the off-board device(s) may programmatically perform one or more operations responsive to detecting the ERP(s). For example, the off-board device(s) may communicate an indication of the detected ERP(s) to the HMD device at 826. Alternatively or additionally, the off-board device(s) may communicate an indication of the detected ERP(s) to the third-party device(s) at 828. At 830, the HMD device may receive the indication of the detected ERP(s) communicated by the off-board device(s) at 826, and may programmatically perform one or more operations responsive to the indication.

Alternatively or additionally, at 832, the third-party device(s) may receive the indication of the one or more ERPs communicated by the off-board device(s) at 828, and may programmatically perform one or more operations responsive to the indication. For example, as indicated at 834, the HMD device may communicate an indication of the detected ERP(s) to the third-party device(s) that reside outside of the HMD system. Furthermore, at 836, the third-party device(s) may receive the indication of the one or more ERPs communicated by the HMD device at 834, and may programmatically perform one or more operations responsive to the indication as previously described at 836.

FIG. 8 further depicts how off-board device(s) of the HMD system, such as remote sensors, may communicate information to the HMD device as depicted at 802. Examples of this information may include sensor information, such as user selections, user inputs, or other user monitoring data captured via sensor devices that are located off-board the HMD device. These user selections or user inputs may correspond to user actions that are observed by the user to elicit ERPs, as an example. While FIG. 8 depicts communications initiated by a sender of certain information, in another implementation, the information may be requested from the sender by the receiving party, such as periodically or responsive to a user request or other user input.

In response to detecting an ERP or receiving indication of a detected ERP, some or all of the following operations may be performed by the HMD device, the off-board device(s), and/or the third-party device(s): (1) storing an indication of the detected ERP in a data storage device, (2) passing the indication of the detected ERP to another process implemented by a computing device or computing system, (3) presenting or initiating presentation of the indicated ERP via an output device to notify a user of the detected ERP, (4) presenting or initiating presentation of a request for additional user input or performance of a user task via an output device, (5) transmitting or initiating transmission of the indication of the detected ERP directed to another computing device or computing system, (6) capturing a pre-defined data set that contains information to be associated with the detected ERP, (7) associating information with an identifier of the ERP to obtain event-associated data, (8) generating an event report for the detected ERP that contains the event-associated data, (9) storing the event report and its event-associated data in a data storage device, (10) presenting or initiating presentation of the event report and its event-associated data via an output device, (11) transmitting or initiating transmission of the event report and its event-associated data directed to one or more subscriber(s) over a communications network, (12) transmitting or initiating transmission of a notification of the ERP directed to one or more subscriber(s) over a communications network, (13) enabling one or more subscriber(s) to request and retrieve, or otherwise access the event report and its event-associated data for the ERP from a data storage device.

In the above example operations, the act of presenting or initiating presentation via an output device, may involve visual, auditory, and/or haptic output by one or more output device(s) of the HMD device, off-board device(s), and/or third-party device(s). For example, one or more graphical content items containing information perceivable by a user may be displayed via the near-eye display(s) of the HMD device or other suitable graphical display device. As another example, a verbal message or other sound perceivable by a user may be generated via one or more audio speaker(s) of the HMD device or other suitable device.

Depending on implementation, some or all of the example operations described above may be programmatically performed by the HMD device, the off-board device(s), and/or the third-party device(s) responsive to detecting the ERP or receiving indication of the detected ERP, such as previously described with reference to operations 814, 820, 822, 824, 830, 832, 836, etc. Furthermore, the specific operation(s) performed in response to an ERP may be based on the ERP component(s) detected for that ERP, as well as the event-associated data.

In an example use-scenarios, ERP-Ne detection may be used within the context of validating whether a human subject has correctly performed a task. If an ERP-Ne component is detected, then the human subject may be have performed an erroneous action with respect to a task. A variety of remedial operations may be performed in response to ERP-Ne detection. Furthermore, these remedial operations may be augmented, discontinued, negated, or selected based on whether a subsequent ERP-Pe component is detected for the same ERP as the ERP-Ne component.

As a first example, a user wearing an HMD device may be presented with visual, auditory, and/or haptic feedback in response to detecting an ERP-Ne component. This feedback may indicate to the user that an ERP-Ne component has been detected. The user may then choose to re-examine the task subject matter in further detail upon receiving such feedback, thereby enabling the user to take corrective action, if necessary. The feedback may further include a request for additional information from the user. For example, the user may be visually presented with one or more augmented reality/mixed reality graphical user interface (GUI) element(s) requesting that the user manually provide a user input to indicate to the HMD system whether the task was or was not correctly performed by the user. The user input provided to the HMD system in response to the request may be stored in association with the ERP-Ne event as event-associated data, enabling subsequent auditing of the user's task proficiency, subject matter knowledge, and accuracy in responding to the inquiry. Furthermore, if a subsequent ERP-Pe component is detected for the same ERP as the ERP-Ne component, then the visual, auditory, or haptic feedback may be negated or may be augmented, discontinued, negated, or selected, depending on implementation. For example, the previously described feedback may be delayed for a period of time to enable the user to take corrective action.

As a second example, responsive to detecting an ERP-Ne component, video and audio captured by a camera (e.g., a forward-facing or outward-facing camera) and microphone of the HMD device and/or by other nearby camera(s) or microphone(s) interfacing with the HMD system may be stored, an identifier of the detected ERP-Ne component may be associated with the saved video/audio, and a notification of the detected ERP-Ne may be transmitted to a subscriber of a notification service of the HMD system, enabling the subscriber to review the video/audio. The video/audio may be reviewed to verify results of the detected ERP-Ne component. Upon verifying that the detected ERP-Ne component pertains to a user error or anomaly, additional inspection may be performed with respect to the subject matter triggering the ERP-Ne component. Furthermore, re-training or other corrective action may be recommended or initiated with respect to the user of the HMD device that generated the ERP-Ne component. Re-training of groups of users may be recommended or initiated for tasks that are associated with high error or anomaly rates as indicated by accumulated ERP-Ne detection data.

Responsive to ERN/FRN detection, the user may be prompted via the HMD device or other client device for verification or reselection for mistakes of which they are aware, an enabling response may be delayed if the user was unaware of the error or anomaly (this would provide the user with time to realize their mistake), and/or the recently-completed iteration of a brain computer interface (e.g., a P300 speller) may be repeated. Knowledge of task error or anomaly rates may also provide supervisors or other third parties with identification of locations or tasks where errors or anomalies are prevalent and/or errors or anomalies by current task and context could inform query presentation. When there is a higher likelihood of error or anomaly, significant aspects of a message to a user may be emphasized. Error or anomaly rates of different user interface designs may be used by their developers to guide user interface design for augmented and mixed reality.

For ERP-MMN, if a user's MMN value and/or skill level does not exceed a threshold level, a notification may be presented to the user (e.g., on the heads-up display) that provides the user with an opportunity to access additional information relating to the context (e.g., task), the user may be presented with augmented work instructions training them on how to perform task, the user may be reassigned to a different task, or the user may be continued to work on the task but may be required to capture verification/validation images or obtain review/approval by another person. Furthermore, other user's having the requisite skill level for that particular task may be assigned the task. Additionally or alternatively, the user's supervisor may be presented with a notification that identifies the user and context, and recommends additional information or training resources to be provided to that user. Such notifications to supervisors or other third-parties may be anonymized with respect to the identity of the user, and the notifications or summaries of results may be combined across a group of users. For example, a workforce of users may be identified as having certain percentage or proportion of novice or expert skill level for a particular task or context, enabling a supervisor or other third-party to implement additional training.

Figure 9:
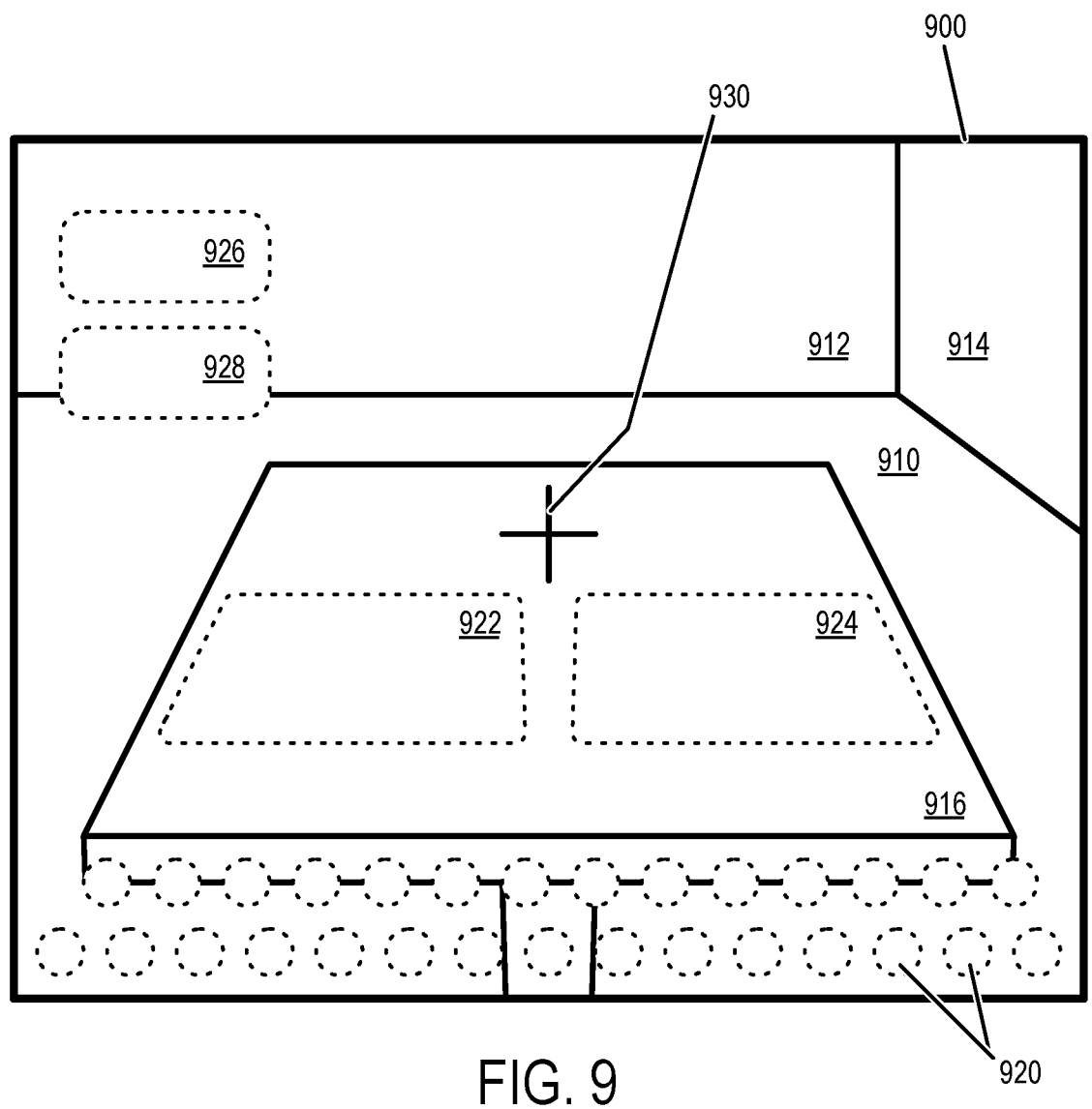
FIG. 9 depicts an example augmented reality or mixed reality view provided by an HMD device.

FIG. 9 depicts an example augmented reality or mixed reality view 900 that may be provided by an HMD device. Within view 900, physical objects that are present in the real-world environment may reside within a field of view of a user of the HMD device. In this example, a floor 910, walls 912 and 914, and a surface of a table 916 represent physical objects of the real-world environment that are present within the user's field of view. Also within view 900, one or more virtual objects may be presented via a graphical display device of the HMD device overlaid upon or integrated with the user's field of view of the real-world environment. In this example, virtual objects 920-928 (depicted in FIG. 9 with broken lines) are presented via a near-eye graphical display of the HMD device. These virtual objects take the form of visual augmented reality or mixed reality content when overlaid upon or integrated with the user's field of view of the real-world environment.

Some virtual objects may be world-locked, meaning that their positioning is defined by a particular positioning within the real-world environment. In this example, virtual objects 922, 924 are world-locked with respect to a surface of table 916 to provide the appearance that the virtual objects 922, 924 are resting upon the surface of the table. Some virtual objects may be view-locked, meaning that their positioning is tied to a particular positioning within the user's field of view that may be independent of an orientation of that field of view within the real-world environment. In this example, virtual objects 926, 928 are view-locked with respect to an upper left-hand corner region of the user's field of view, and a set of virtual objects 920 are view-locked with respect to a lower region of the user's field of view. The set of virtual objects 920 may, for example, represent a typing or spelling interface (e.g., a virtual keyboard) containing a plurality of alpha/numeric characters and/or related controls for generating human-readable text information.

Virtual objects, such as previously described virtual objects 920-928, may be presented by the HMD device as graphical elements that may include text, images, video, color, shading, textures, multi-dimensional models, menus, etc. Virtual objects may be two-dimensional or three-dimensional, static or dynamic, have a fixed position or may move relative to the user's field of view or real-world environment, depending on implementation or context. For example, a virtual object may take the form of a multi-dimensional graphical object (e.g., a two or three-dimensional object) having a six degree-of-freedom (6DOF) positioning (e.g., X, Y, Z values) and/or orientation (e.g., yaw, pitch, roll values) within a coordinate system within the user's field of view. Virtual objects may be selectable by a user to interact with the HMD device, the HMD system, or other suitable entity. Virtual objects, when graphically presented, may convey information that may be visually perceived by the user, such as through text information, color-coded information, imagery, etc. Such information may be context-specific and may be displayed, discontinued, updated, or otherwise varied in appearance by the HMD device based on context. For example, virtual objects may be selectively presented by the HMD device as visual stimulus that elicits ERPs from the user that may be detected by EEG interfaces located on-board the HMD device.

A virtual object presented via the HMD device may be targeted for selection by a user using a variety of techniques. Such techniques may include reticle-based targeting, eye tracking, and/or the use of peripheral pointing devices that interface with the HMD device. Non-limiting examples of these techniques are discussed in further detail below.

As a first example, a near-eye graphical display or see-through visor of the HMD device may include a reticle or other suitable sighting indicator (indicated schematically at 930) that aids the user in selection of graphical content presented via the HMD device. The reticle may take the form of a physical sighting indicator that is present upon or within a see-through graphical display or visor of the HMD device. In this implementation, the reticle as a physical sighting indicator is located at a fixed position that is view-locked to the user's field of view. Alternatively, the reticle may take the form of a graphical object presented via the graphical display of the HMD device, typically in a fixed position within the user's field of view in a view-locked implementation. The reticle, in combination with inertial sensors on-board the HMD device, may provide the user with the ability to target and select a virtual object that is presented via the HMD device or a physical object that is within the user's field of view. A dwell-based selection technique may be used enable the user to select the targeted object by aiming the reticle at the object, and maintaining that aim upon the object for at least a threshold period of time. Alternatively or additionally, an input device of the HMD device or a peripheral device interfacing with the HMD device may be used by the user to provide a selection command. Examples of such input devices include handheld devices that include a button or touch-sensitive input interface that may be actuated by the user to provide a selection command and/or a microphone on-board the HMD device by which a spoken selection command may be provided by the user.

As another example, eye tracking may be performed by the HMD device via an on-board ocular camera to determine a gaze vector of the user's eye. Eye tracking may be achieved using a variety of techniques. For example, an infrared (IR) light source located on-board the HMD device may emit IR that is projected upon the eye of the user. The IR may be used to illuminate features of the eye and/or produce a glint upon reflective surfaces of the eye, which may be captured by the ocular camera. A comparison of the relative positioning of these features of the eye and the reflected IR (e.g., glint) may be analyzed by the HMD device to identify or otherwise estimate a gaze vector of the user. In eye tracking implementations, the previously described reticle may be optionally omitted. A dwell-based selection technique may be used enable the user to select the targeted object by directing the user's gaze upon an object, and maintaining that gaze upon the object for at least a threshold period of time. A selection command may be generated with respect to an object in response to the user looking at the object, such that the user's gaze vector intersects the object, and in some implementations maintaining the gaze vector upon the object for at least a threshold period of time. Alternatively or additionally, an input device of the HMD device or a peripheral device interfacing with the HMD device may be used by the user to provide a selection command. Examples of such input devices include handheld devices that include a button or touch-sensitive input interface that may be actuated by the user to provide a selection command and/or a microphone on-board the HMD device by which a spoken selection command may be provided by the user.

As yet another example, a handheld device interfacing with the HMD device may take the form of a pointing device that enables a user to control a location of a selector icon (e.g., a pointer) presented via the graphical display of the HMD device. The selector icon may take the form of previously described sighting indicator 930, as an example. The handheld device may include one or more buttons, touch-sensitive interfaces, etc. In this implementation, the selector icon may move relative to the user's field of view in response to positioning commands provided by the user via the handheld device. Examples of pointing devices include a computer mouse, handheld controller, touch-sensitive interface, etc. Once an object has been targeted by the user moving the selector icon to the object, a selection command may be provided by the user to select that object. A selection command may be provided via the handheld device or other suitable user input device, such as a microphone as a spoken selection command.

FIG. 10 depicts an example head mounted display (HMD) device 1000 that is wearable upon a head of a human subject (i.e., a user). HMD device 1000 includes a device body 1010. Device body 1010, in this example, includes a helmet 1012 that is wearable by a user. Helmet 1012 includes a transparent or see-through visor 1014 that enables the user to view a real-world environment through the visor. However, HMD device 1000 may take other suitable forms, such as a headband, glasses, hat, or other suitable wearable form factor.

HMD device 1000 includes a see-through graphical display system 1040 (i.e., a see-through display) having one or more see-through display panels upon or within which computer-generated graphical content (e.g., one or more virtual objects) may be presented to a user while wearing the HMD device. Display subsystem 1040 is an example of a near-eye graphical display device that is mounted upon device body 1010 of the HMD device. In some examples, HMD device 1000 may include two or more see-through display panels or two or more independent display regions of a common see-through display panel, to provide independent graphical displays to each eye of the user.

In a first example, see-through graphical display system 1040 may include two side-by-side see-through display panels 1042 corresponding to a right eye and a left eye of the user. FIG. 10 depicts additional aspects of this example configuration. Alternatively a single see-through display panel 1042 may have two side-by-side display panel regions corresponding to a right eye and left eye of the user. See-through display panel(s) 1042 may include or take the form of reflective optical waveguides that receive light projected by one or more light projectors 1044, and reflect or otherwise direct at least a portion of that light towards the eyes of the user. For example, each display panel or display panel region thereof may receive light from a respective light projector. See-through display panel(s) 1042 may additionally or alternatively include or take the form of lenses that reflect or otherwise direct at least a portion of the light received from light projector(s) 1044 towards the eyes of the user.

In a second example, see-through graphical display system 1040 may omit see-through display panel(s) 1042, and one or more see-through display panels may be instead integrated into visor 1014. One or more display regions (indicated schematically at 1016) of visor 1014 may each include or take the form of a reflective optical waveguide that receives light projected by one or more light projector(s) 1044, and reflects that light back towards the eye or eyes of the user. The relative positioning of light projector(s) 1044 in FIG. 9 is represented schematically with respect to see-through display panel(s) 1042. As such, it will be understood that light projector(s) 1044 may reside at other suitable positions for projecting light onto or into see-through display panel(s) 1042, or alternatively onto or into see-through display region(s) 1016 of visor 1014.

A user, while wearing HMD device 1000, is permitted to view the real-world environment through the see-through display panel(s) of see-through graphical display system 1040. Graphical content, such as represented schematically at 1018 within the context of a visor-integrated see-through display panel, may optionally be presented by the HMD device. This graphical content may be sized and/or positioned relative to physical objects within the real-world environment to provide the appearance of the graphical content being physically present within the real-world environment. Alternatively or additionally, graphical content presented via the see-through graphical display may take the form of informational content that is not necessarily aligned with physical objects within the real-world environment.

HMD device 1000 may further include a variety of on-board sensors. As a non-limiting example, HMD device 1000 may include optical sensors, such as a forward facing camera 1050 and an ocular camera 1052. Forward facing camera 1050 may be configured and otherwise oriented to capture at least a portion of a field of view (some, all, or a greater field of view) of the user as the HMD device is worn upon the head of the user. Images or other optical sensor measurements captured by forward facing camera 1050 may be used by the HMD device, for example, to assist in aligning graphical content with physical features present within the real-world environment. Ocular camera 1052 may be oriented generally rearwards, towards an eye of the user. Images or other optical sensor measurements captured by ocular camera 1052 may be used by the HMD device, for example, to track a gaze direction of the user's eye or to otherwise measure features of the user's eye.

Additional on-board sensors include a set of spatially distributed EEG interfaces 1060, represented schematically in FIG. 10. Each EEG interface may include a non-invasive electrode that interfaces with a control subsystem of the HMD device via one or more wired electrical contacts. Electrodes 1062, 1064, and 1066 are depicted in FIG. 10, as examples of EEG interfaces 1060. Electrodes of EEG interfaces 1060 are typically located along an inner-facing surface of helmet 1012 or other wearable cap or band that covers at least a portion of the head of the user. In this example, HMD device 1010 includes a head strap 1032 that is adjustable to fit the size of the user's head, thereby providing a snug fit that brings the electrodes of the EEG interfaces into contact with or close proximity to a scalp or skin of the user.

While HMD devices are described herein within the context of see-through displays that provide a direct view of the real-world environment, it will be understood that the methods and techniques described herein may be implemented within the context of HMD devices that do not include a see-through display, but instead provide a live view of the real-world environment via an on-board camera (e.g., forward facing camera 150) and graphical display device.

FIG. 11 depicts additional aspects of an HMD device 1100. HMD device 1100 is a non-limiting example of previously described HMD device 1000 of FIG. 10. Within FIG. 11, HMD device 1100 is presented in a head-on view in contrast to the side view of HMD device 1000 depicted in FIG. 10. HMD device 1100 again takes the form of a helmet having a visor in this example. Here, a helmet 1102 of HMD device 1100 may include a variety of sensors such as forward facing camera 1108 and/or audio sensors 1110 (e.g., provided at the front, back, and/or a top section 1106 of helmet 1102). See-through display panels 1112 are separate from or independent of visor 1104 in this example, and are mounted to helmet 1102 via a body 1114. Helmet 1102 further includes rearward facing ocular cameras 1111 mounted thereon. Each ocular camera 1111 is directed to a respective eye of the user to capture an image of the iris, retina, pupil, or other eye components. Each ocular camera 1111 may be positioned on helmet 1102 above and/or to the side of each eye, and facing a corresponding eye. Helmet 1102 also includes a set of spatially distributed EEG interfaces 1160 to observe brain activity of the user, including non-invasive electrodes 1162, 1164, 1166, 1168, etc.

Figure 12:
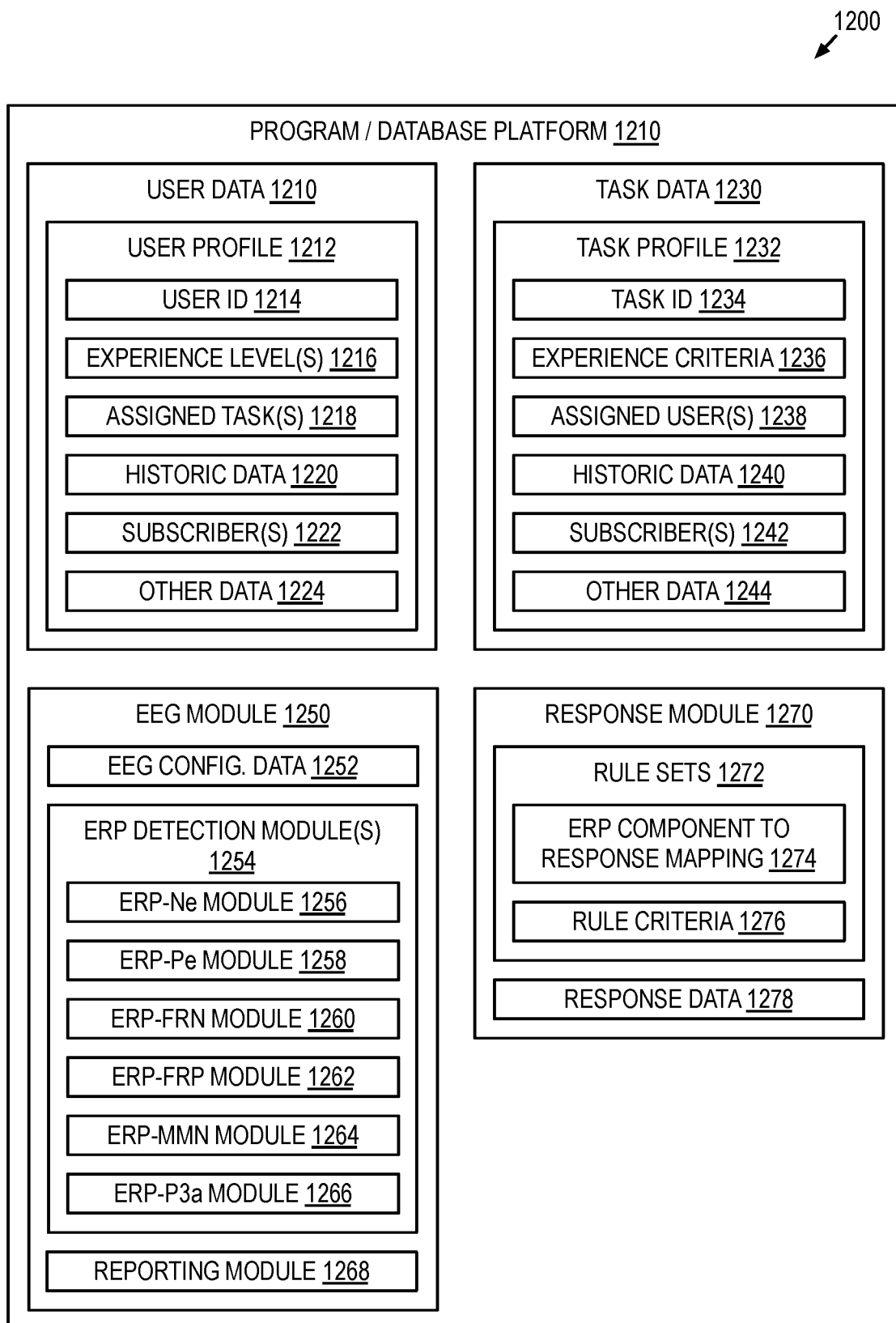
FIG. 12 is a schematic diagram depicting an example program/database platform.

FIG. 12 is a schematic diagram depicting an example program/database platform 1200. Platform 1200 may include computer executable instructions and/or data that may form one or more programs and/or database systems that are implemented by a computing device or computing system containing two or more computing devices. For example, platform 1200 may reside at an HMD device (or other client computing device) or may span two or more computing devices, such as an HMD device and one or more off-board device(s) of an HMD system.

In this example, platform 1200 includes user data 1210, task data 1230, EEG module 1250, and response module

1270. Typically, user data 1210 and task data 1230 are implemented as one or more databases of a database system stored at a data storage device. EEG module 1250 and response module 1270 are typically implemented as computer program components.

User data 1210 may include one or more user profiles corresponding to respective users of the platform. An example user profile 1212 for a particular user is depicted in FIG. 12. User profile 1212 includes a user identifier 1214, a set of skill level(s) 1216, a set of assigned task(s) 1218, historic data 1220, a set of subscriber(s) 1222, and other data 1224. User identifier 1214 refers to a particular user of the platform and enables that user to be distinguished from other users of the platform. The set of skill level(s) 1216 may include one or more skill levels that are associated with the user. In some examples, multiple skill levels may be assigned with the user in which each skill level pertains to a different task type or subject. Each skill level assigned to the user may be one of a plurality of assignable skill levels (e.g., novice or expert). The set of assigned task(s) 1218 may include one or more tasks that are associated with the users. These tasks may correspond to tasks that are defined by task data 1230. Historic data 1220 may include some or all data obtained by the platform with respect to the user, in raw and/or processed forms. The set of subscriber(s) 1222 may include one or more subscribers that are to receive reports, notifications, or other information updates relating to the user. Subscribers may include supervisors, administrators, the user itself, or other subscribers. Subscribers may be represented by a user name and/or contact address (email address, etc.) that enables and directs the platform to communicate information concerning the user to the subscriber.

Task data 1230 may include one or more task profiles corresponding to respective tasks that may be assigned to users of the platform. An example task profile 1232 for a particular task is depicted in FIG. 12. Task profile 1232 includes a task identifier 1234, a set of skill level criteria 1236, a set of assigned user(s) 1238, historic data 1240, a set of subscriber(s) 1242, and other data 1244. Task identifier 1234 refers to a particular task established by a supervisor, administrator, or other user of the platform, and enables that task to be distinguished from other tasks established for the platform. The set of skill level criteria 1236 may define to a minimum threshold skill level for users to be assigned to that task. As previously described, each skill level assigned to the user may be one of a plurality of assignable skill levels (e.g., novice or expert), and these skill levels may be defined on a per-task basis. The set of assigned user(s) 1238 may include one or more users (e.g., represented by user identifiers) that are associated with the tasks. These users may be defined within the platform and/or identified by user data 1210. Historic data 1240 may include some or all data obtained by the platform with respect to the task, in raw and/or processed forms. The set of subscriber(s) 1242 may include one or more subscribers that are to receive reports, notifications, or other information updates relating to the task. Subscribers may include supervisors, administrators, the user that initiated or performed the task, or other subscribers. As previously described, subscribers may be represented by a user name and/or contact address that enables and directs the platform to communicate information concerning the task to the subscriber.

EEG module 1250 includes EEG configuration data 1252 and ERP detection module(s) 1254, and reporting module 1268. EEG configuration data 1252 includes data that defines a spatial relationship between or among the EEG interfaces of a particular hardware configuration. For example, EEG configuration data 1252 may define a spatial relationship for a set of EEG interfaces of an HMD device or other device. The spatial relationship may be defined, at least in part, with reference to the previously described 10-20 system. However, other suitable frameworks may be used. In an example, each electrode of an EEG interface may be assigned an identifier that is further associated with a spatial positioning identifier that identifies a location relative to a head of human subject.

ERP detection module(s) 1254 includes one or more modules that are configured to detect a particular ERP component. For example, ERP detection module(s) 1254, to detect ERP components within a set of EEG signals, may include: ERP-Ne module 1256 to detect the ERP-Ne component, ERP-Pe module 1258 to detect the ERP-Pe component, ERP-FRN module 1260 to detect the ERP-FRN component, ERP-FRP module 1262 to detect the ERP-Pe component, ERP-MMN module 1264 to detect the ERP-MMN component, ERP-P3a module 1266 to detect the ERP-P3a component, etc. In at least some implementations, ERP detection module(s) may be developed, at least in part, by training the ERP detection module(s) on EEG data for their respective ERP components using a set of EEG interfaces that corresponds to or is sufficiently similar in spatial configuration to the EEG interfaces (e.g., of an HMD device or other suitable wearable device) as described by EEG configuration data 1252. EEG module 1250 may further include a reporting module 1268 that communicates an indication of a detected ERP or ERP component to another entity and/or associates event-related information with the ERP to obtain event-associated data. The reporting provided by reporting module 1268 may be responsive to or based on the rule sets and other data of response module 1270.

Response module 1270 may include rule sets 1272 and response data 1278. Rule sets 1272 may include an ERP component to response mapping 1274 that directs the platform how to response to detection of particular ERP components. Rule sets 1272 may define the programmatic operations that are performed in response to detection of particular ERP components. Rule sets 1272 may further include rule criteria that defines trigger conditions for performing such programmatic operations. Response data 1278 may include information that defines the type of response and/or the content of that response. For example, response data 1278 may define whether a response includes visual, auditory, and/or haptic information, as well the content of the response.

Figure 13B:
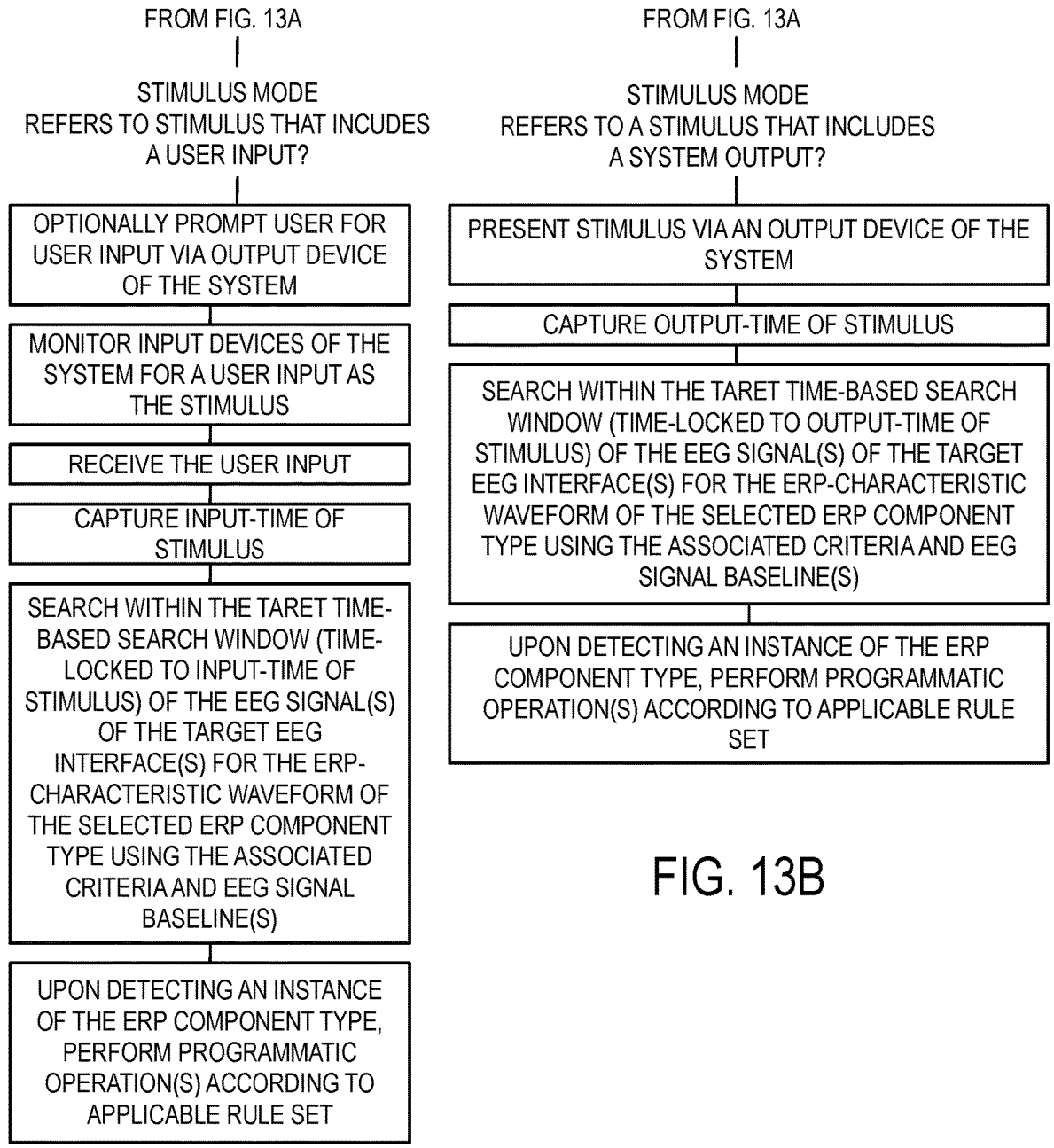

FIGS. 13A and 13B is a flow diagram depicting an example method that may be implemented with respect to detection of ERP components. The method of FIGS. 13A and 13B may be implemented by a computing device or computing system of the previously described HMD device or HMD system. This method or portions thereof may be performed in combination with the other methods, processes, and operations described herein.

The various computing devices or computing systems described herein may incorporate one or more logic device(s), and one or more data storage device(s). A logic device includes one or more physical hardware devices configured to execute instructions. Such instructions are executable by the logic device to implement or otherwise perform the various methods or operations described herein. For example, a logic device may be configured to execute instructions that are part of one or more applications, services, programs, routines, libraries, objects, components, data structures, or other logical constructs. Such instructions may be implemented to perform a task or function, implement a data type, transform the state of one or more components, achieve a technical effect, or otherwise arrive at a desired result. A logic devices may include one or more processors configured to execute software instructions. Additionally or alternatively, a logic device may include one or more hardware or firmware logic machines configured to execute hardware or firmware instructions. Processors of a logic device may be single-core or multi-core, and the instructions executed thereon may be configured for sequential, parallel, and/or distributed processing. Individual components of a logic device may be distributed among two or more separate devices (e.g., an HMD device and an off-board device of an HMD system), which may be remotely located and/or configured for coordinated processing. Aspects of the logic device may be virtualized and executed by remotely accessible, networked computing devices configured in a cloud-computing configuration.

Data storage devices include one or more physical memory devices (e.g., non-transitory memory devices) configured to hold instructions executable by the logic devices to implement the methods or operations described herein. When such methods or operations are implemented, a state of the data storage devices may be transformed—e.g., to hold different data. Data storage devices may include removable and/or built-in devices. Data storage devices may include optical memory devices, semiconductor memory devices, and/or magnetic memory devices, among other suitable forms. Data storage devices may include volatile, nonvolatile, dynamic, static, read/write, read-only, random-access, sequential-access, location-addressable, file-addressable, and/or content-addressable devices.

Aspects of logic devices and data storage devices may be integrated together into one or more hardware-logic components. While a data storage device includes one or more physical hardware devices, aspects of the instructions described herein alternatively may be, at times, propagated by a communication medium (e.g., an electromagnetic signal, an optical signal, etc.) that is not held by a physical device for a finite duration.

It is to be understood that the configurations and/or approaches described herein are exemplary in nature, and that these examples are not to be considered in a limiting sense, because numerous variations are possible. The specific routines or methods described herein may represent any number of processing strategies. As such, the various acts illustrated may be performed in the sequence illustrated, in other sequences, in parallel, or in some cases omitted. Likewise, the order of the above-described processes may be changed without departing from the scope of the present disclosure.

The subject matter of the present disclosure includes all novel and nonobvious combinations and sub-combinations of the various processes, systems and configurations, and other features, functions, acts, and/or properties disclosed herein, as well as any and all equivalents thereof. It should be understood that the disclosed embodiments are illustrative and not restrictive. Variations to the disclosed embodiments that fall within the metes and bounds of the claims, now or later presented, or the equivalence of such metes and bounds are embraced by the claims.

The invention claimed is:

1. A head mounted display (HMD) system, comprising:
   an HMD device wearable on a head of a user, the HMD device including:
      a device body,
      a near-eye graphical display device mounted upon the device body to present graphical content to the user,
      a user input device having a user input interface, and
      a set of spatially distributed electroencephalography (EEG) interfaces mounted upon the device body, each EEG interface including an electrode that observes fluctuations of an electrical potential at a respective location relative to the head of the user; and
   a computing system including at least one on-board computing device that is mounted upon the device body, the computing system programmed to:
      receive a user input from the user via the user input interface, responsive to receiving the user input, output a stimulus for presentation to the user via an output device of the HMD device, the stimulus describing an attribute of the user input,
      following presentation of the stimulus, obtain a set of EEG signals via the set of EEG interfaces, each EEG signal indicating the fluctuations in the electrical potential observed by a respective EEG interface;
      based on one or more of the EEG signals of the set of EEG signals, detect an event-related potential (ERP) event that includes either a feedback-related negativity (ERP-FRN) component or a feedback-related positivity (ERP-FRP) component, by:
         identifying a stimulus-time value for the presentation of the stimulus,
         determining a target time range for observing the ERP-FRN or ERP-FRP within a feedback-defined time period subsequent to the stimulus-time value,
         identifying a FRN-characteristic fluctuation or a FRP-characteristic fluctuation in electrical potential observed via an EEG interface within the target time range; and
      responsive to the identifying of the FRN-characteristic fluctuation representing an error or anomaly contained within the user input received via the user input interface, presenting a user interface element via the near-eye graphical display device that enables the user to change the user input to obtain an updated user input via the user input interface; or
      otherwise, responsive to the identifying of the FRP-characteristic fluctuation, accepting the user input at a process operating at the HMD system.

2. The HMD system of claim 1, wherein the computing system further includes at least one off-board computing device that communicates with the computing device over a wireless communications network; and
   wherein the computing system is further programmed to transmit an indication of a detected ERP-FRN from the computing device to the at least one off-board computing device over the wireless communications network.

3. The HMD system of claim 1, wherein the FRN-characteristic fluctuation and the FRP-characteristic fluctuation in the electrical potential are observed via an EEG interface located at or near a fronto-central location relative to the head of the user; and
   wherein the feedback-defined time period is 140-300 milliseconds subsequent to the stimulus-time value.

4. The HMD system of claim 1, wherein an error-related component (ERC) of the ERP event is an error-related negativity (ERP-Ne) component of the ERP event; and
   wherein the computing system is programmed to output the indication of the ERC by outputting an indication of an error or anomaly being associated with the action for presentation via the near-eye graphical display device.

5. The HMD system of claim 1, wherein an error-related component (ERC) of the ERP event is an error-related negativity (ERP-Ne) component of the ERP event; and
wherein the computing system is programmed to identify an ERC-characteristic fluctuation by identifying an Ne-characteristic fluctuation in the electrical potential detected via the EEG interface or near a frontal location (Fp) or a fronto-central location (Fz) relative to the head of the user.

6. The HMD system of claim 5, wherein an ERC-defined time period is an Ne-defined time period of 80-150 milliseconds subsequent to the stimulus-time value.

7. The HMD system of claim 1, wherein the computing system is further programmed to:
responsive to the identifying of the FRN-characteristic fluctuation, outputting a stimulus to the user via an output device of the HMD system, the stimulus representing an error or anomaly in an action performed by the user, the stimulus including at least one of a visual, oral, or haptic stimulus.

8. The HMD system of claim 1, wherein an error-related component (ERC) of the ERP event is an error-related positivity (ERP-Pe) component of the ERP event.

9. The HMD system of claim 8, wherein the computing system is further programmed to:
identifying a Pe-characteristic fluctuation in the electrical potential detected via an EEG interface located at or near a central location relative to the head of the user.

10. The HMD system of claim 1, wherein an ERC-defined time period is a Pe-defined time period of 200-500 milliseconds subsequent to the stimulus-time value.

11. The HMD system of claim 1, wherein the computing system is further programmed to:
transmitting the indication of a detected ERC from the computing device to an off-board computing device over a wireless communications network.

12. The HMD system of claim 1, wherein an error-related component (ERC) of the ERP event is an error-related negativity (ERP-Ne) component of the ERP event, and wherein the computing system is further programmed to:
determining a magnitude of a deflection in the fluctuations in electrical potential for the ERP-Ne component; and
outputting an indication of the magnitude of the deflection.

13. The HMD system of claim 1, wherein the detecting of the event-related potential (ERP) event further comprises:
for each EEG signal in the set of EEG signals, identifying an error-related component (ERC)-characteristic fluctuation in the electrical potential within that EEG signal;
responsive to identifying the ERC-characteristic fluctuation, outputting an indication of a detected ERC and an event-time value for the detected ERC;
for the detected ERC, determining a target time range for observing an action performed by the user within an ERC-defined time period prior to the event-time value; and
outputting the target time range associated with the indication of the detected ERC.

14. The HMD system of claim 13, wherein an ERC of the ERP event is an error-related negativity (ERP-Ne) component of the ERP event;
wherein the identifying of the ERC-characteristic fluctuation includes identifying an Ne-characteristic fluctuation in the electrical potential observed via an EEG interface located at or near a frontal location or a fronto-central location relative to the head of the user; and
wherein the ERC-defined time period is an Ne-defined time period of 80-150 milliseconds prior to the event-time value associated with the Ne-characteristic fluctuation.

15. The HMD system of claim 1, wherein an error-related component (ERC) of the ERP event is an error-related positivity (ERP-Pe) component of the ERP event; and
wherein the computing system is programmed to identify an ERC-characteristic fluctuation includes identifying a Pe-characteristic fluctuation in the electrical potential observed via an EEG interface located at or near a central location relative to the head of the user; and
wherein the ERC-defined time period is a Pe-defined time period of 200-500 milliseconds prior to the event-time value associated with the Pe-characteristic fluctuation.

16. The HMD system of claim 1, wherein the computing system is further programmed to:
identify a target action from among a set of observed actions performed by the user based on the target time range associated with an indication of an error-related component (ERC); and
output an indication of the target action.

17. The HMD system of claim 1, wherein the computing system is further programmed to output an indication of a target action by presenting the indication of the target action via the near-eye graphical display device.

18. The HMD system of claim 1, wherein the computing system is further programmed to output an indication of a target action by transmitting the indication of the target action from the on-board computing device to an off-board computing device over a wireless communications network.

* * * * *